(12) United States Patent
Morré et al.

(10) Patent No.: US 7,491,413 B2
(45) Date of Patent: Feb. 17, 2009

(54) COMPOSITIONS AND METHODS FOR TREATING AND PREVENTING VIRUS INFECTIONS

(75) Inventors: D. James Morré, West Lafayette, IN (US); Dorothy M. Morré, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 167 days.

(21) Appl. No.: 11/241,744

(22) Filed: Sep. 30, 2005

(65) Prior Publication Data

US 2007/0077316 A1    Apr. 5, 2007

(51) Int. Cl.
*A61K 36/82* (2006.01)
*A61K 36/81* (2006.01)
*A61K 31/35* (2006.01)
*A61K 31/05* (2006.01)

(52) U.S. Cl. .................. 424/729; 424/760; 514/456; 514/732; 514/738

(58) Field of Classification Search ..................... None
See application file for complete search history.

(56) References Cited

U.S. PATENT DOCUMENTS

| | | | |
|---|---|---|---|
| 5,569,673 A | 10/1996 | Morré et al. | |
| 5,605,810 A | 2/1997 | Morré et al. | |
| 5,670,520 A * | 9/1997 | Gelfand et al. | 514/314 |
| 6,410,052 B1 | 6/2002 | Morré et al. | |
| 6,410,061 B1 | 6/2002 | Morré et al. | |
| 6,428,818 B1 | 8/2002 | Morré et al. | |
| 6,528,489 B1 * | 3/2003 | Papathanassiu | 514/14 |
| 6,593,371 B1 * | 7/2003 | Staggs | 514/627 |
| 6,652,890 B2 | 11/2003 | Morré et al. | |
| 6,759,064 B2 * | 7/2004 | Morre et al. | 424/729 |
| 7,192,612 B2 * | 3/2007 | Morre et al. | 424/729 |
| 2001/0051184 A1 * | 12/2001 | Heng | 424/461 |
| 2003/0215462 A1 * | 11/2003 | Wacher et al. | 424/195.18 |

FOREIGN PATENT DOCUMENTS

WO      WO 95/26743      10/1995

OTHER PUBLICATIONS

Evans, A. Viral Infections of Humans—Epidemiology and Control. 1989. Third Ed. Publisher: Plenum Medical Book Co., New York, NY, pp. 68, 564-565, 687-704, 713-721.*
Morre et al. J. Pharm. Phamacol. 2003. vol. 55, No. 7, pp. 987-994, SCISEARCH Abstract enclosed.*
Matsubara et al. Biochem. Biophys. Res. Commun. 2003. vol. 310, No. 3, pp. 715-719, DRUGU Abstract enclosed.*
Yagiz et al. FASEB J. 2003. vol. 17, No. 4-5, Abstract No. 457.5, BIOSIS Abstract enclosed.*
Abell et al. (Sep. 1993) "Sindbis Virus Membrane Fusion is Mediated by Reduction of Glycoprotein Disulfide Bridges at the Cell Surface," *J. Virol.* 67:5496-5501.
Adelson et al. (1999) "Inhibition of Human Immunodeficiency Virus (HIV-1) Replication in SupT1 Cells Transduced with and HIV-1 LTR-Driven PKR cDNA Construct," *Eur. J. Biochem.* 264:806-815.
Bardwell et al. (Sep. 1993) "The Bonds that Tie: Catalyzed Disulfide Bond Formation," *Cell* 74:769-771.
Battini et al. (Feb. 1995) "Receptor-Binding Domain of Murine Leukemia Virus Envelope Glycoproteins," *J. Virol.* 69:713-719.
Brightman et al. (1992) "A Growth Factor- and Hormone-Stimulates NADH Oxidase from rat Liver Plasma Membrane," *Biochim. Biophys. Acta.* 1105:109-117.
Bruno et al. (1992) "Stimulation of NADH Oxidase Activity from Rat Liver Plasma Membranes by Growth Factors and Hormones is Decreased or Absent with Hepatoma Plasma Membranes," *Biochem. J.* 284:625-628.
Caterina et al. (1991) "The Vanilloid Receptor: A Molecular Gateway to the Pain Pathway," *Ann. Rev. Neurosci.* 24:487-517.
Chivers et al. (1996) "The CXXC Motif: Imperatives for the Formation of Native Disulfide Bonds in the Cell," *EMBO J.* 15:2659-2667.
Dehahn et al. (1997) "NADH Oxidase Activity Present on Both External and Internal Surfaces of Soybean Plasma membranes," *Biochim. Biophys. Acta.* 1328:99-108.
Freedman, R.B. (Jun. 1989) "Protein Disulfide Isomerase: Multiple Roles in the Modification of Nascent Secretory Proteins," *Cell* 57:1069-1072.
Kishi et al. (1999) "The Plasma Membrane NADH Oxidase of HeLa Cells has Hydroquinone Oxidase Activity," *Biochim. Biophys. Acta.* 1412:66-77.

(Continued)

*Primary Examiner*—Christopher R. Tate
(74) *Attorney, Agent, or Firm*—Greenlee, Winner and Sullivan, P.C.

(57) ABSTRACT

Provided are compositions comprising a vanilloid and tea catechins in amounts and proportions which combat virus infections in a human or animal. The vanilloid can be provided in the form of a dried pepper preparation and the tea catechins can be provided in the form of a green tea extract (or concentrate). These active ingredients can be provided separately or in combination. The administration of a such nutritional or other composition, desirably oral administration (in an amount effect) results in reduced virus infection or ameliorated symptoms of virus infection in a human or an animal in need of such a composition.

8 Claims, 35 Drawing Sheets

OTHER PUBLICATIONS

Madani et al. (Dec. 1998) "An Endogenous Inhibitor of Human Immunodeficiency Virus in Human Lymphocytes is Overcome by the Viral Vof Protein," *J. Virol.* 72:10251-10255.

Mitscher et al. (1994) "Chemoprotection: A Review of the Potential Therapeutic Antioxidant Properties of Green Tea (*Camellia sinensis*) and Certain of its Constituents." *Med. Res. Rev.* 17:327-365.

Mizuno, T. (1992) "Inhibitory Effect of Tannic Acid Sulfate and Related Sulfates on Infectivity, Cytopathic Effect, and Giant ell Formation of Human Immunodeficiency Virus," *Planta Medica* 5:535-539.

Morré et al. (2000) "Preferential Inhibition by (–)-Epigallaocatechin-3-Gallate of the Cell Surface NADH Oxidase and Growth of transformed Cells in Culture," *Biochem. Pharmacol.* 60:937-946.

Morré, D.J. (1998) "NADH Oxidase: A Multifunction Ectoprotien of the Eukaryotic Cell Surface," In: *Plasma Membrane Redox Systems and Their Role in Biological Stress and Disease*, Asard et al. Eds., Kluwar Academic Publishers, Dordrecht, The Netherlands, pp. 121-156.

Morré et al. (1997) "A Protein Disulfide-Thiol Interchange Activity of HeLa Plasma Membranes Inhibited by the Antitumor Sulfonylurea N-(4-methylphenylsulfonyl)-N'-(4-chlorophenyl) Urea," *Biochim. Biophys. Acta* 1325:117-125.

Morré et al. (1998) "Effect of the Quassinoids Glaucarubolone and Simalikalactone D on Growth of Cells Permanently Infected with Feline and Human Immunodeficiency Viruses and on Viral Infections," *Life Sci.* 62:231-219.

Morré et al. (1994) "Inhibition by Brefeldin A of NADH Oxidation Activity of Rat Liver Golgi Aparatus Accelerated by GDP," *FEBS Lett.* 346:199-202.

Morré, D.J. (1994) "Hormone- and Growth Factor-Stimulated NADH Oxidase," *Biorg. Biomemb.* 26:625-628.

Morré et al. (1995) "Mechanism of Killing HeLa Cells by the Antitumor Sulfonyluea, N-(4-methylphenylsulfonyl)-N'-(4-chlorophenyl) Urea (LY181984)," *Protoplasma* 184:188-195.

Morré et al. (Mar. 1995) "Capsaicin Inhibits Preferentially the NADH Oxidase and Growth of Transformed Cells in Culture," *Proc. Nat. Acad. Sci. USA* 92:1831-1835.

Morré et al. (1995) "The Antitumor Sulfonylurea N-(4-methylphenylsulsonyl)-N'-(4-chlorophenyl) urea (Ly181984) Inhibits NADH Oxidase Activity of HeLa Plasma Membranes," *Biochim. Biophys. Acta.* 1240:11-17.

Morré et al. (1996) "Capsaicin Inhibits Plasma Membrane NADH Oxidase Growth of Human and Mouse Melanoma Lines," *Eur. J. Can.* 32A:1995-2003.

Morré et al. (1997) "Is the Drug-Responsive NADH Oxidase of the Cancer Cell Plasma Membrane a Molecular Target for Adriamycin," *J. Bioeng. Biomemb.* 29:269-280.

Mukoyama et al. (1991) "Inhibition of Rotavirus and Enterovirus Infections by Tea Extracts," *Jpn. J. Med. Sci. Biol.* 44:181-186.

Nakane et al. (1990) "Differential Inhibitory Effects of Some Catechin Derivatives on the Activities of Human Immunodeficiency Virus Reverse Transcriptase and Cellular Deoxyribonucleic and Ribonucleic Acid Polymerase," *Biochem.* 29:2841-2845.

Nakayama et al. (Aug. 1993) "Inhibition of the Infectivity of Influenza Virus by Tea Polyphenols," *Antiviral Res.* 21:289-299.

Paulik et al. (1999) "Drug-Antibody Conjugates with Anti-HIV Activity," *Biochem. Pharmacol.* 58:1781-1790.

Ryser et al. (May 1994) "Inhibition of Human Immunodeficiency Virus Infection by Agents that Interfere with Thiol-Disulfide Interchange Upon Virus-Receptor Interaction," *Proc. Nat. Acad. Sci. USA* 91:4559-4563.

* cited by examiner

Fig. 6

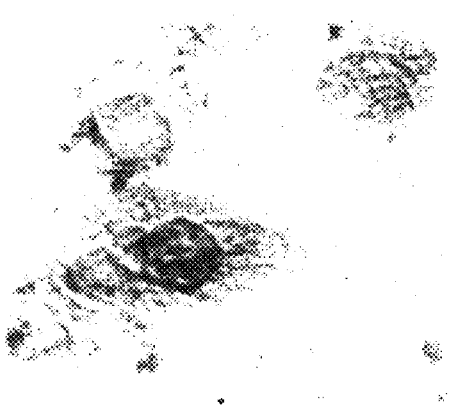 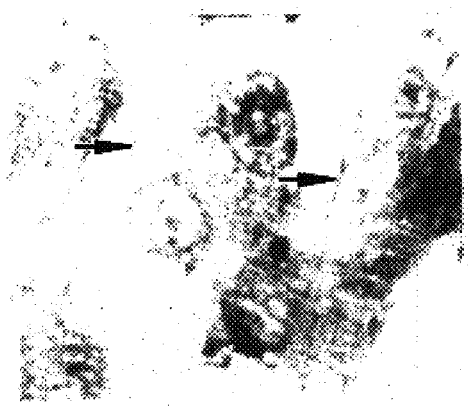
FIG. 14A　　　　FIG. 14B

COMPOSITIONS AND METHODS FOR TREATING AND PREVENTING VIRUS INFECTIONS

CROSS-REFERENCE TO RELATED APPLICATIONS

Not Applicable.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

The present invention relates to novel methods and compositions which utilize catechins including, but not limited to, epigallocatechin-3-gallate (EGCg), epicatechin (EC), epicatechin gallate (ECG), and epigallocatechin (EGC), which are found in varying levels in tea leaves, in combination with vanilloids including, but not limited to, vanillylamine, the vanilloid head group of capsaicin. The compositions of the invention contain various amounts of the catechins and vanilloids, and optionally, other therapeutic agents. The invention also encompasses the varying modes of administration of the catechins and vanillbids as a dietary or nutritional supplement or as a therapeutic compound. There have been reports of antiviral activities of catechins (Mitscher et al., 1994, Med. Res. Rev. 17: 327-365). Inhibition by EGCg and epicatechin-3-gallate (ECG) of both reverse transcriptase at 10 to 20 ng/ml and RNA polymerase has been reported (Nakano & Ono, 1990, Biochemistry 29: 2841-2845; Mizuno, 1992, Planta Medica 5: 535). The effect appeared to be unrelated to anti-oxidant action, but it seemed to correlate with competition for the template-primer. However, the concentrations of these two catechins required to produce the antiviral effects were toxic to whole cells in culture.

EGCg also has demonstrated a protective effect against infection of cultured rhesus monkey kidney MA104 cells with rotaviruses and enteroviruses (Mukoyama et al., 1991, Jpn. J. Med. Sci. Biol. 44: 181-186). To be most effective, it was necessary to treat the virus with EGCg prior to infection. Treatment of the cells themselves with EGCg either before or after infection produced lesser effects.

Decreased inhibition of infectivity of influenza A and influenza B viruses in cultured Madin-Darby canine kidney cells by EGCg was observed by Nakayama et al.; it was attributed to inhibition of virus adsorption to the target cells and overall agglutination of virus, both as determined by electron microscopy (Nakayama et al., 1993, Jpn. Antiviral Res. 21: 289).

The basis for the anti HIV activity of EGCg in the present is unknown. However, previous work from our laboratory has identified a tumor- (cancer-) associated growth protein, tNOX, as a target for EGCg, the principal anticancer tea catechin, to help explain the anticancer benefits of tea (Morré et al., 2000, Biochem. Pharmacol. 60: 937-946). One of the catalytic activities of this protein that is blocked by EGCg is that of protein disulfide interchange (PDI) (Morré, 1998, Plasma Membrane Redox Systems and their Role in Biological Stress and Disease, Kluwer Academic Publishers, Dordrecht, N L, pp. 121-156).

Enveloped mammalian viruses generally enter cells via fusion of viral and cellular membranes (Battini et al., 1995, J. Virol. 69: 713-719). Thiol-disulfide interchange reactions occur during the interaction of viruses with cells, and these interactions may be necessary for fusion of viral and cellular membranes (Ryser et al., 1994, Proc. Natl. Acad. Sci. USA 91: 4559-4563; Abell & Brown, 1993, J. Virol. 57: 5496-5501). For example, Sindbis virus-induced fusion of cells was enhanced by exogenous reducing agents and inhibited by thiol alkylating agents (Abell & Brown, 1993, J. Virol. 67: 5496-5501). The explanation offered was based on a model in which virion binding to cells led to reduction of critical disulfide bonds in the Sindbis envelope proteins. The result was suggested to be an increased flexibility required for fusion of viral and cellular membranes.

Infection of lymphoid cells by HIV-1 was inhibited by membrane impermeant sulfhydryl blocking reagents and by inhibitors of cell surface PDI (Ryser et al., 1994, Proc. Natl. Acad. Sci. USA, 91: 4559-5463). Implicit in the findings of Ryser et al. (1994, Proc. Natl. Acad. Sci. USA, 91: 4559-5463) was the interpretation that the PDI-like activity mediates a thiol-disulfide exchange with HIV-1 envelope proteins, triggering changes in conformation required for HIV-1 entry.

Demonstrations of the thiol interchange activity of the NOX proteins included the restoration of activity to reduced, denatured and oxidized (scrambled) yeast RNase through reduction, refolding under non-denaturing conditions and reoxidation to form a correct secondary structure stabilized by internal disulfide bonds. The activity resembled that of a classical PDI of the endoplasmic reticulum (Freedman, 1989, Cell 57: 1069-1072) but was clearly due to an activity of a different protein. The EGCg-responsive protein disulfide-thiol interchange activity was not altered by the presence of antisera to PDI (Morré et al., 1997, Biochim. Biophys. Acta 1325: 117-125). Ineffective in blocking tNOX activity were a mouse monoclonal antibody (SPA-891, StressGen Biotechnologies) to PDI from bovine liver (cross-reactive with PDI from human, monkey, rat, mouse and hamster cell lines) and a peptide antibody directed to the characteristic cys-X-X-cys motif common to most, if not all, members of the PDI family of proteins (Chivers et al., 1996, EMBO J. 15: 2659-2667; Bardwell and Beckwith, 1993, Cell 74: 769-771). The EGCg-inhibited NADH oxidation site of the cell surface-located drug-inhibited protein disulfide-thiol interchange protein is located at the external cell surface (Morré et al., 1998, Life Sci. 62: 213-219) and is inhibited by other drugs such as quassinoids (Morré et al., 1994, FEBS Lett. 346: 199-202), brefeldin A (Paulik et al., 1999, Biochem. Pharmacol. 58: 1781-1790) and quassinoid conjugates (Morré, 1995, Biochim. Biophys. Acta 1240: 201-208) all with documented activity in blocking or slowing HIV infection.

Vanilloids are the active ingredients found in *Capsicum* species, cayenne pepper, black pepper, paprika, cinnamon, clove, mace, mustard, ginger, turmeric, papaya seed and the cactus-like plant *Euphorbia resinifera*. Vanilloid compounds have been generally disclosed to have analgesic, anti-irritant and anti-inflammatory activities, although certain capsaicinoids are irritants. It is believed that vanilloids mediate their biological effects through vanilloid receptors (reviewed by Caterina & Julius, 2001, Annu. Rev. Neurosci. 24:487-517). *C. annuum* varieties include the guajillo, cayenne, bell, poblano, serrano, jalapeno, and New Mexican/Anaheim peppers, among others. Representative *Capsium frutescens* include the Tabasco pepper and the African bird pepper. The especially pungent peppers can be treated with amidase and optionally also with food grade hydrolases, prior to formulation with the tea extracts. Such treatment reduces the apparent "heat" of the pepper preparation and reduces the potential discomfort after consumption.

Capsaicinoids are found in extracts of the fruit (peppers) of the *Capsicum* species, with high amounts being found in the pungent chili peppers. The capsaicinoids represent a group of natural products that are vanillylamides of monocarboxylic acids of varying chain lengths from C-8 to C-11 with varying degrees of unsaturation.

A unique family of plasma membrane NADH oxidases (NOX), hydroquinone oxidase and protein disulfide-thiol interchange activities (ECTO-NOX-Proteins) that is responsive to hormone and growth factors has been identified (Brightman et al., 1992, Biochim. Biophys. Acta 1105:109-117; Morré, 1994, J. Bioenerg. Biomemb. 26:421-433; and Morré, 1998, Plasma Membrane Redox Systems and their Role in Biological Stress and Disease, Kluwer Academic Publishers, Dordrecht, N L, pp. 121-156). Further, a hormone-insensitive and drug-responsive form of NOX designated tNOX which is specific to cancer cells has been reported (Bruno et al., 1992, Biochem. J. 284:625-628; Morré and Morré, 1995, Protoplasma 184:188-195; Morré et al., 1995, Proc. Natl. Acad. Sci. U.S.A. 92:1831-1835; Morré et al., 1995, Biochim. Biophys. Acta 1240:11-17; Morré et al., 1996, Eur. J. Can. 32A:1995-2003; and Morré et al., 1997, J. Biomemb. Bioenerg. 29:269-280; U.S. Pat. Nos. 5,569,673 and 5,605,810).

Because the ECTO-NOX proteins are located at the external plasma membrane surface and are not transmembrane, primary functional roles as NADH oxidases is not considered likely (Morré, 1994, J. Bioenerg. Biomemb. 26:421-433; DeHahn et al., 1997, Biochim. Biophys. Acta 1328:99-108; and Morré, 1998, Plasma Membrane Redox Systems and their Role in Biological Stress and Disease, Kluwer Academic Publishers, Dordrecht, N L, pp. 121-156). The oxidation of NADH provides for a convenient method to assay the activity. However, the ultimate physiological electron donor is most probably hydroquinones. Specific activities for hydroquinone oxidation are greater than or equal to those of NADH oxidation and/or protein thiol-disulfide interchange (Kishi et al., 1999, Biochim. Biophys. Acta 1412:66-77).

A constitutive CNOX form was originally defined as a drug-indifferent ECTO-NOX activity associated with the plasma membrane of non-transformed cells that was the normal cell's counterpart to tNOX (Morré, 1998, 26:421-433; DeHahn et al., 1997, Biochim. Biophys. Acta 1328:99-108; and Morré, 1998, Plasma Membrane Redox Systems and their Role in Biological Stress and Disease, Kluwer Academic Publishers, Dordrecht, N L, pp. 121-156). Indeed, a 36 kDa protein isolated from rat liver and from plants has NOX activity that is unresponsive to tNOX inhibitors (Brightman et al., 1992, Biochim. Biophys. Acta 1105:109-117).

There is a longfelt need in the art for a safe and effective nutritional supplement for treating, reducing the incidence of and/or preventing viral infections, including the common cold.

BRIEF SUMMARY OF THE INVENTION

The invention encompasses compositions comprising catechins and vanilloids in ratios that result in synergistic properties for preventing viral disorders and/or for ameliorating the symptoms of virus infection in a human or animal in need (exposed to virus or suffering from virus infection). These compositions are useful for the prevention and treatment of viral infections or as a dietary or nutritional supplement that protects white blood cells and maintains healthy blood levels thereof. Specific therapeutic regimens, pharmaceutical compositions, nutritional (and/or dietary) supplement compositions and kits are also provided by the invention.

In one embodiment, a nutritional supplement described herein comprises the administration of catechins in combination with vanilloids, to a mammal (human or animal) as a dietary supplement. In a preferred embodiment, the mammal is a human. The catechins are provided in the form of a dehydrated, decaffeinated green tea extract (food grade or beverage grade) and the vanilloids are provided as a composition of dried ground *Capsicum annuum* fruits having a thin pericarp and a moderate content of capsaicin (between 2 and 4 on the heat scale of 1-10, Scoville heat units 2,500 to 5,000).

In another embodiment, the invention described herein comprises the administration of a therapeutically effective amount of catechins in combination with vanilloids, to a mammal in need of antiviral therapy or prevention or reduction in the incidence or severity of viral infection. In a preferred embodiment, the mammal is a human. The sources of the catechins and vanilloids can be as described above. In another embodiment, the invention further encompasses the use of additional therapeutic agent(s) in combination therapy to treat viral infections, for example, zinc chloride, zinc gluconate, vitamin C and/or sodium selenate.

In a specific embodiment, the catechins comprise epigallocatechin-3-gallate (EGCg), epicatechin gallate (ECG), epigallocatechin (EGC), epicatechin (EC) or a combination thereof, in combination with one or more vanilloids, such as, but not limited to, vanillylamine. In a preferred embodiment, the ratio of EC to EGCg concentration in the tea catechins is from about 10:1 to about 1000:1. The ratio of geen tea extract to *Capsicum* powder is desirably from about 100:1 to about 80:1, desirably from about 25:1 to about 50:1.

The compositions of the present invention are based on, at least in part, the discovery that catechins, vanilloids, and other anti-cancer therapeutic agents, inhibit the activity of an ECTO-NOX protein (vNOX) which is specific to virus infected cells and necessary for virus infection. The inhibition of vNOX results in the prevention of viral infection, and ultimately, apoptosis of the infected cell, whereas normal cells (which lack vNOX but instead express the isoforms CNOX) are not affected. Thus, the invention provides a potent therapeutic effect with reduced or no adverse effects on normal, healthy cells.

BRIEF DESCRIPTION OF THE DRAWINGS

FIG. 6: Dose response of HRV 14 cytopathic effects on Hela cells to the logarithm of CapsiVirol-T concentration (in the media) 72 h after infection. The $EC_{50}$ was about 20 nM (range 2 to 50 nM).

FIG. 14A-14B: Cytochemical localization using the antibody to the conserved c-terminal adenine nucleotide binding region of tNOX of a tNOX-like determinant at the cell surface of uninfected (FIG. 14A) and HRV 14-infected (24 h) (FIG. 14B) MCF-10A cells. Detection was with horseradish peroxidase tagged second antibody and deposition of oxidized diaminobenzidine. The reaction products were black. Infected cells show blackened borders (arrows). Cell borders of uninfected cells are not visible. No counterstain was added.

Figure 25:
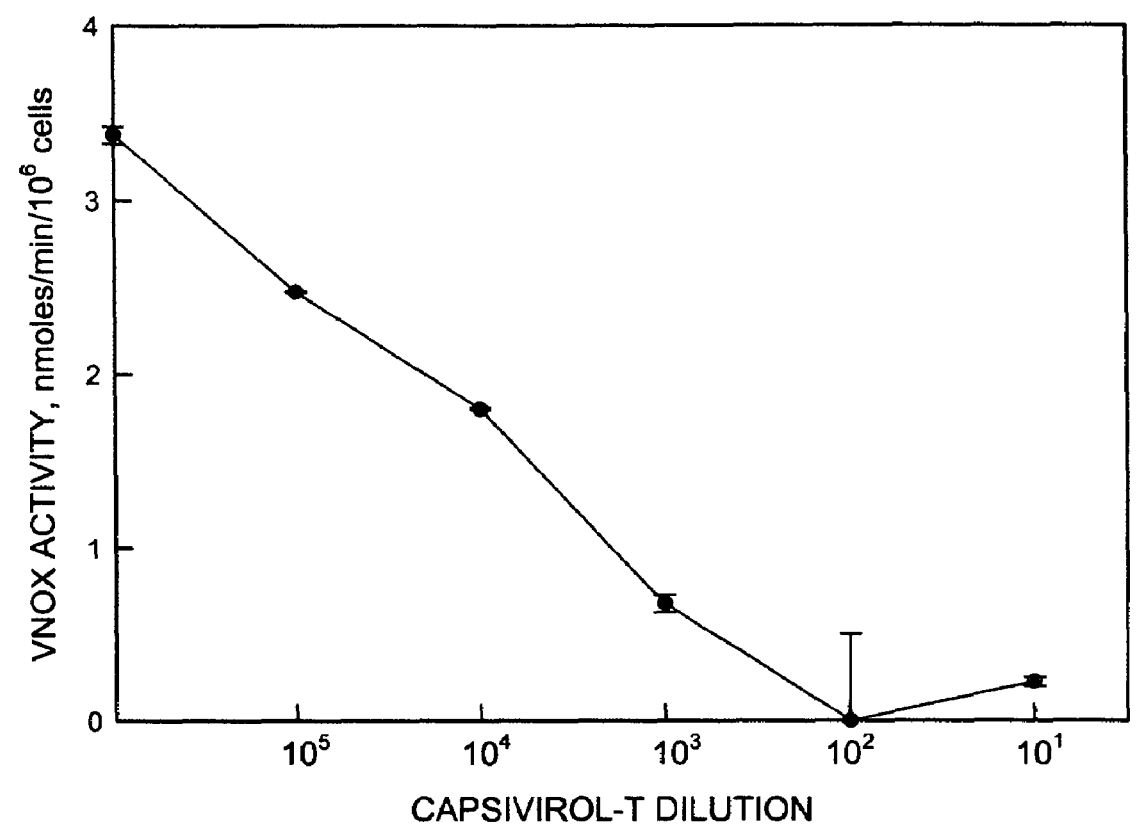

FIG. 25: Inhibition of HRV 14-induced vNOX activity of infected (72 h) MCF-10A cells as a function of CapsiVirol-T dilution of 1:10,000 (=10 nM EGCg).

FIG. 27: Plaque-forming units/ml of BHK cells infected with yellow fever virus as a function of the logarithm of CapsiVirol-T concentration. The concentrations required to block virus production were high compared to those required to block the cytopathic effects of HRV in HeLa or hFOB (osteoblast) cells. The results shown are the average of three experiments.

DETAILED DESCRIPTION OF THE INVENTION

Figure 1:
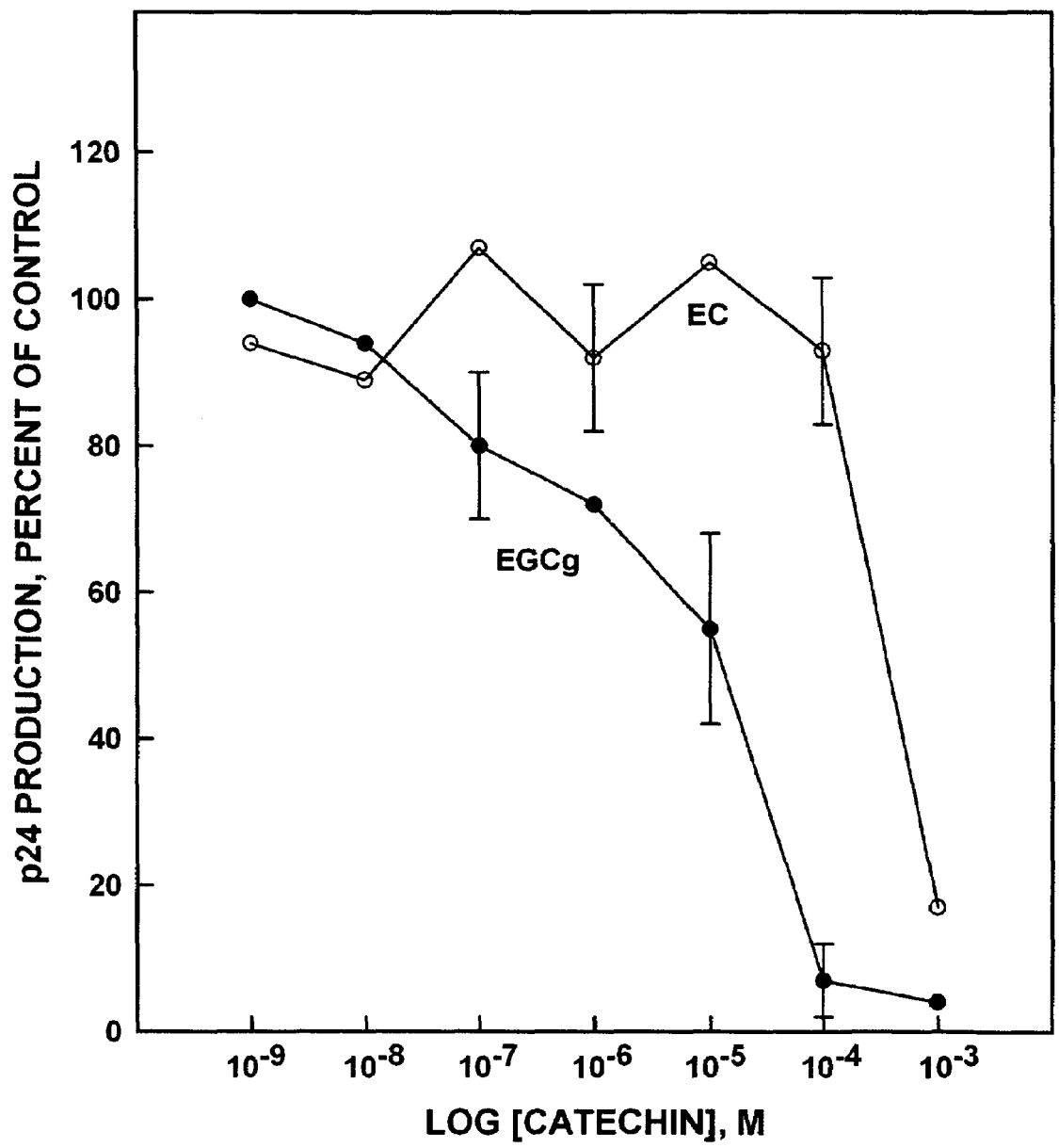
FIG. 1: HIV-1 replication in MT-2 cells as scored by p24 antigen production in the presence of (−)-epigallocatechin-3-gallate (EGCg) and (−)-epicatechin (EC), as described herein below. Average of 3 to 4 independent experiments, each as a fourfold assay. Standard deviations are given when more than 2 experiments per concentrations were done. Supernatant p24 antigen production was measured after 4 or 5 d of culture.

A category of ECTO-NOX activity associated exclusively with viral infection, designated vNOX, is described for the first time herein. vNOX is the catechin-vanilloid target which accounts for the activity and subsequent synergy of catechin-vanilloid mixtures in viral prevention and therapy.

The invention encompasses compositions comprising catechins and vanilloids in ratios that result in synergistic inhibition of infection of mammalian cells by viruses, thus reducing viral infections and/or ameliorating the symptoms of a virus infection. The compositions are useful for the prevention and treatment of viral infections or as a dietary or nutritional supplement that protects white blood cells and maintains healthy blood levels of white blood cells. Therapeutic regimens and nutritional supplements are provided herein.

Catechins can be administered in combination with vanilloids, in therapeutically effective ratios and amounts of the combination to a mammal as a dietary (nutritional) supplement for an improvement in health, especially to reduce the incidence and/or severity of virus infections. In a preferred embodiment, the mammal is a human.

In another embodiment, the invention described herein comprises the administration of a therapeutically effective amount of catechins in combination with vanilloids, to a mammal in need of antiviral therapy or prevention. In a preferred embodiment, the mammal is a human. In another embodiment, the invention further encompasses the use of additional therapeutic agent(s) in combination therapy to prevent, reduce incidence or treat viral infections, especially in combination with a salt of zinc or selenium safe for human consumption.

In a specific embodiment, the catechins comprise epigallocatechin-3-gallate (EGCg), epicatechin gallate (ECG), epigallocatechin (EGC), epicatechin (EC) or a combination thereof, in combination with one or more vanilloids, such as, but not limited to, vanillylamine. In a preferred embodiment, the ratio of EC to EGCg concentration in the tea catechins is from about 10:1 to about 1000:1. The source of vanilloids can be a *Capsicum*, preferably a dried *Capsicum* preparation, an amidase-treated *Capsicum* preparation, safe for human consumption. The preferred chiles are those with a thin pericarp and low sugar content that can be finely powdered by milling and with a moderate capsaicin content of between 2 and 4 on the heat scale of 1-10, Scoville heat units 2,500 to 5,000. The especially pungent peppers can be treated with amidase and optionally also with food grade hydrolases prior to formulation with the tea extracts. Such treatment reduces the apparent "heat" of the pepper preparation and the potential discomfort after consumption.

Catechins, vanilloids, and other anti-cancer therapeutic agents, inhibit the activity of an ECTO-NOX protein, vNOX, specific to virus infected cells, and necessary for virus infection. The inhibition of vNOX reduces or prevents viral infection, and ultimately, apoptosis of the infected cell, whereas normal cells (which lack VNOX but instead express the isoforms CNOX) are not affected. Thus, the compositions of the present invention provide a potent therapeutic effect with reduced or no adverse effects on normal, healthy cells.

The catechins and target proteins defined herein are abbreviated as follows: (±)-catechin, C; (−)-epicatechin, EC; gallocatechin, GC; gallocatechin gallate, GCG; (−)-epigallocatechin, EGC; (−)-epicatechin gallate, ECG; (−)-epigallocatechin-3-gallate, EGCg; nicotinamide adenine dinucleotide, NADH; cell surface hydroquinone (NADH) oxidase with protein disulfide-thiol isomerase activity, ECTO-NOX; ECTO-NOX present in both non-cancer and cancer cells, CNOX; ECTO-NOX specific to cancer cells, tNOX; ECTO-NOX specific to virus-infected cells, vNOX. $EC_{50}$ is the concentration which reduces CPE by 50% in infected cells.

The present invention relates to compositions and methods for treatment and prevention of viral disorders. Specifically exemplified viruses which are responsive include, without limitation, rhinovirus and HIV. The protective effect has also been seen for other viruses including influenza A and B and herpes viruses.

The invention is based, in part, on the discovery that vanillylamine, the head group of capsaicin, and catechins, in tea, synergistically inhibit the activity of an isoform of NADH oxidase (ECTO-NOX) that is specific to virus-infected cells. A synergy between green tea and vanillylamine was observed in the inhibition of vNOX activity. An unexpected result described herein was the synergy between catechin-containing green tea extracts and vanilloid-containing *Capsicum* preparations including, but not limited to, dried ground pepper powders from dried fruits of *Capsicum annuum* and/or *Capsicum fructescens* with respect to virus infection.

In one embodiment, the invention provides a composition comprising tea catechins and vanilloids. In another embodiment, the invention provides a pharmaceutical composition comprising tea catechins, vanilloids and a pharmaceutical carrier or carrier or filler useful in a nutritional supplement. In yet another embodiment, the invention provides a dietary supplement or nutritional composition comprising tea catechins and vanilloids.

In a specific embodiment, the catechins comprise eipgallocatechin gallate (EGCg), epicatechin gallate (ECG), epigallocatechin (EGC), and epicatechin (EC) or a combination thereof, including food or beverage grade tea concentrates, in combination with one or more vanilloids, including at least one food grade preparation of *Capsicum* powder.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be inclusive. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, compositions and starting materials, other than those specifically exemplified can be employed in the practice of the invention without resort to undue experimentation. All art-known functional equivalents, of any such methods, starting materials, synthetic methods, and formulation strategies are intended to be included in this invention. Whenever a range is given in the specification, for example, a concentration range, a time range, or a composition range, all intermediate ranges and subranges, as well as all individual values included in the ranges given are intended to be included in the disclosure.

As used herein, comprising is synonymous with including, containing, or characterized by, and is inclusive or open-ended and does not exclude additional, unrecited elements or method steps. As used herein, consisting of excludes any element, step, or ingredient not specified in the claim element. As used herein, consisting essentially of does not exclude materials or steps that do not materially affect the basic and novel characteristics of the claim. Any recitation herein of the term comprising, particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions to exclude any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art.

In general the terms and phrases used herein have their art-recognized meaning, which can be found by reference to standard texts, journal references and contexts known to those skilled in the art.

The exact formulation, route of administration and dosage can be chosen by the supplier (see e.g. Fingl et al., in The Pharmacological Basis of Therapeutics, 1975, Ch. 1 p. 1).

It should be noted that the supplier would know how to best formulate the product for maximum stability and shelf life to optimize oral availability including sustained release and a standard dosage amount. The magnitude of an administered dose in the management of the disorder of interest varies with the type or severity of the condition to be treated and to the route of administration. The severity of the condition may, for example, be evaluated, in part, by standard prognostic evaluation methods. Further, the dose and perhaps dose frequency, varies according to the age, body weight, and response of the individual patient. Similar considerations apply to veterinary nutrition and medicine.

Depending on the specific conditions being treated and the targeting method selected, such agents may be formulated and administered orally, systemically or locally. Techniques for formulation and administration are known to the art. However, in the instant case, suitable routes include, for example, oral, intragastric, or intestinal administration; but topical, mucosal or parenteral delivery, including intramuscular, subcutaneous, or intramedullary injections, as well as intrathecal, intravenous, or intraperitoneal injections, can be accomplished. The preferred mode of administration is oral, for example, by tablets, capsules, elixirs and the like.

Use of pharmaceutically acceptable or edible carriers to formulate the compounds herein disclosed for the practice of the invention into dosages suitable for oral administration is within the scope of the invention. With proper choice of carrier and suitable manufacturing practice, the compositions of the present invention, in particular those formulated as solutions, may be administered as nutritional supplements. Appropriate compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated. Compositions for topical administration, for example for the treatment of cold sores or genital herpes, are also within the ordinary skill of those in the relevant art.

Pharmaceutical compositions suitable for use in the present invention include compositions wherein the active ingredients are contained in an effective amount to achieve the intended purpose. Determination of the effective amounts is well within the capability of those skilled in the art, especially in light of the detailed disclosure provided herein. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical and/or nutritional supplement preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical and/or nutritional supplement preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

One skilled in the art would readily appreciate that the present invention is well adapted to carry out the objects and obtain the ends and advantages mentioned, as well as those inherent therein. The vanilloid and catechin compounds and methods described herein are representative of preferred embodiments are exemplary and are not intended as limitations on the scope of the invention. Changes therein and other uses will occur to those skilled in the art, which are encompassed within the spirit of the invention, are defined by the scope of the claims.

All references cited herein are hereby incorporated by reference to the extent there is no inconsistency with the present disclosure. The references cited herein indicate the relative level of skill in the relevant arts.

Although the description herein contains certain specific descriptions and examples, these should not be construed as limiting the scope of the invention but as merely providing illustrations of some of the presently preferred embodiments, of the invention. For example, thus the scope of the invention should be determined by the appended claims and their equivalents, rather than by the examples given.

EXAMPLES

Example I (−)-Epigallocatechin-3-Gallate has Anti-Hiv Activity

The MT-2 cell line, which cells are retrovirus transformed, was used. Virus applied to the MT-2 cells was the HXB II standard virus strain of HIV, isolated early in the 1980's (HIV Research Community Standard Reference Gene Sequence Data Base No. 135829). Stock virus was grown on SupT1 cells in RPMI 1640 supplemented with L-glutamine, 10% FCS and gentamicin 10 µg/ml (RPMI supp). The main characteristic of the HXBII virus strain was to induce syncytia (SI) in certain cells such as MT-2 cells. This permitted assessment of the production of HIV by light microscopy, and thus, by titration of supernatant, the amount of infectious virus.

As non-permanent cells, PBM cells were derived from freshly prepared pooled buffy coats from healthy blood donors. The PBM cells were isolated by Ficoll density gradient centrifugation and cultivated (stimulated with phytohemagglutinin) for 48 h in RPMI 1640 medium supplemented with 20% FBS and L-glutamine. PBMC tropic laboratory isolate No. 9.5 was used in the PBMC assays.

Virus replication was determined as follows. Antiviral activity was assessed at day four or five after infection by scoring p24 antigen production by a commercial kit (DuPont) and by titration of the supernatants. Each well of each concentration of compound was titrated in a fourfold assay. MT-2 cells ($4 \times 10^5$ per well) were added to all titration steps. After incubation, 100 µl of supplemented RPMI 1640 was added. After 5 d, all wells were scored for SI formation by light microscopy. The highest dilution (titer) displaying at least one SI were scored as positive, and the highest titers were averaged. The averaged titers of the virus controls were set as 100% and the virus replication in the presence of the compounds were given in % of the controls. Both MT-2 cell and PBM cell supernatants were titered on MT-2 cells.

Cell viability was assessed by determination of the activity of mitochondrial dehydrogenase from the reduction of MTT dye (3-(4,5-dimethylthiazol-2-yl)-2,5-diphenyltetrazolium bromide). After 5 days, 20 µl of MTT stock solution (7.5 mg/ml) was added. Incubation was for 14 h, 37° C., 5% $CO_2$. Subsequently, 100 µl of 10% v/v Triton X100 in acidified isopropanol was added, and absorbance was determined at 550 nm with reference at 630 nm.

The cytotoxic effect of EGCg was reflected by a decrease of the cell viability of mock infected cells in the presence of EGCg in comparison to mock infected cells without EGCg (OD 492 nm) was lower than the value of mock infected cells without EGCg. The cytotoxicity values are given as negative values. Positive values are recorded for a stimulatory effect on cell viability and/or an increase in cell proliferation.

Testing the antiviral potency of various compositions was accomplished as follows. EGCg and EC were from Sigma (St. Louis, Mo.). Stock solutions of 100 mM were prepared in ethanol and serially diluted with water between $10^{-3}$ molar and $10^{-9}$ molar. The compounds at the dilutions indicated were preincubated for 1 h at 37° C. with $0.4 \times 10^5$ MT-2 cells per well in RPMI in a 96 well microtiter system. Subsequently, HXBII standard virus was added and incubated for 4 or 5 d. Each experiment was in a fourfold assay. The residual ethanol was determined to be without effect on cell viability or virus infectivity and production.

Infectivity of HIV in human MT-2 cells grown in culture or in peripheral blood monocytes (PBMCs) obtained from healthy donors was reduced significantly by EGCg. P24 was chosen as a marker for cumulative virus production (viable and non-viable virus) over the 4 or 5 d of cultivating HIV on MT-2 cells or on PBMC. For all concentrations below $10^{-4}$ M, we observed for the control compound EC no virus inhibiting properties, but for EGCg, a 93% inhibition of virus production as compared to the virus control was achieved at $10^{-4}$ M (FIG. 1). For the concentration of $10^{-5}$ M, a 45% inhibition of virus replication was observed which is a difference of 50% compared to EC and represents approximately the $ID_{50}$ for EGCg p24 production. Even for lower concentrations of $10^{-6}$ and $10^{-7}$ M, an inhibitory effect of approximately 20% was seen. At 1 nM there was no effect.

Figure 2:
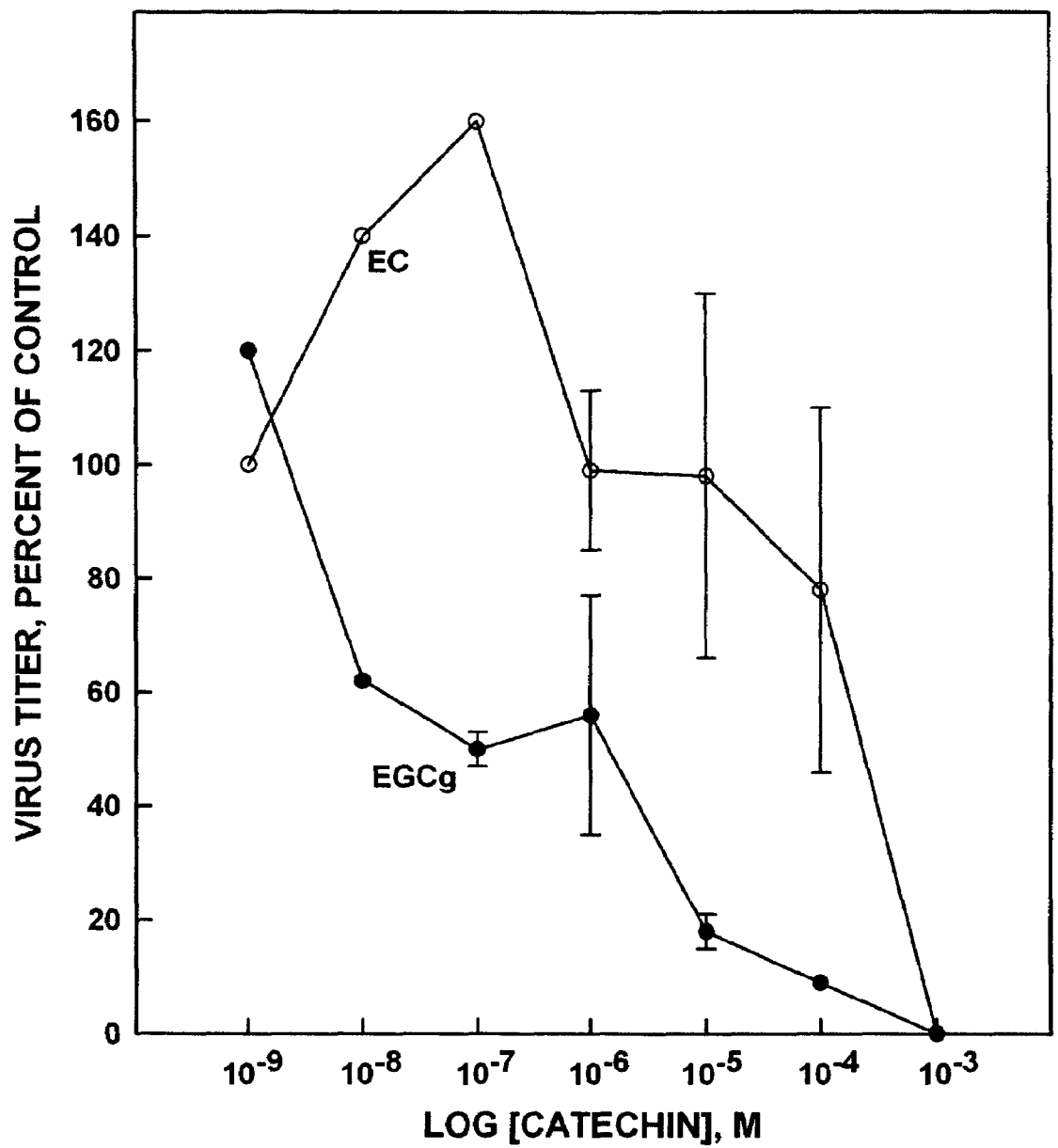
FIG. 2: HIV-1 virus replication in MT-2 cells scored by titration in the presence of (−)-epigallocatechin-3-gallate (EGCg) or (−)-epicatechin (EC), as described herein below. Average of 3 to 4 independent experiments, each as a fourfold assay. Standard deviations are given when more than 2 experiments per concentrations were done. The supernatant virus titer after 4 or 5 d of culture.

Scoring virus replication by determining titres to measure viable, infectious virus, we obtained for $10^{-4}$ M results similar as in the p24 experiments. However, for the concentration of $10^{-5}$ M, titrated virus reached far less levels than p24 antigen. Only 20% of the virus control or EC control was measured. At $10^{-6}$ and $10^{-7}$ M, the reduction was approximately 50%, representing the $ID_{50}$ for EGCg for titers. At $10^{-8}$ M, reduction of titers was still 40% but at 1 nM no reduction was observed (FIG. 2).

Figure 3:
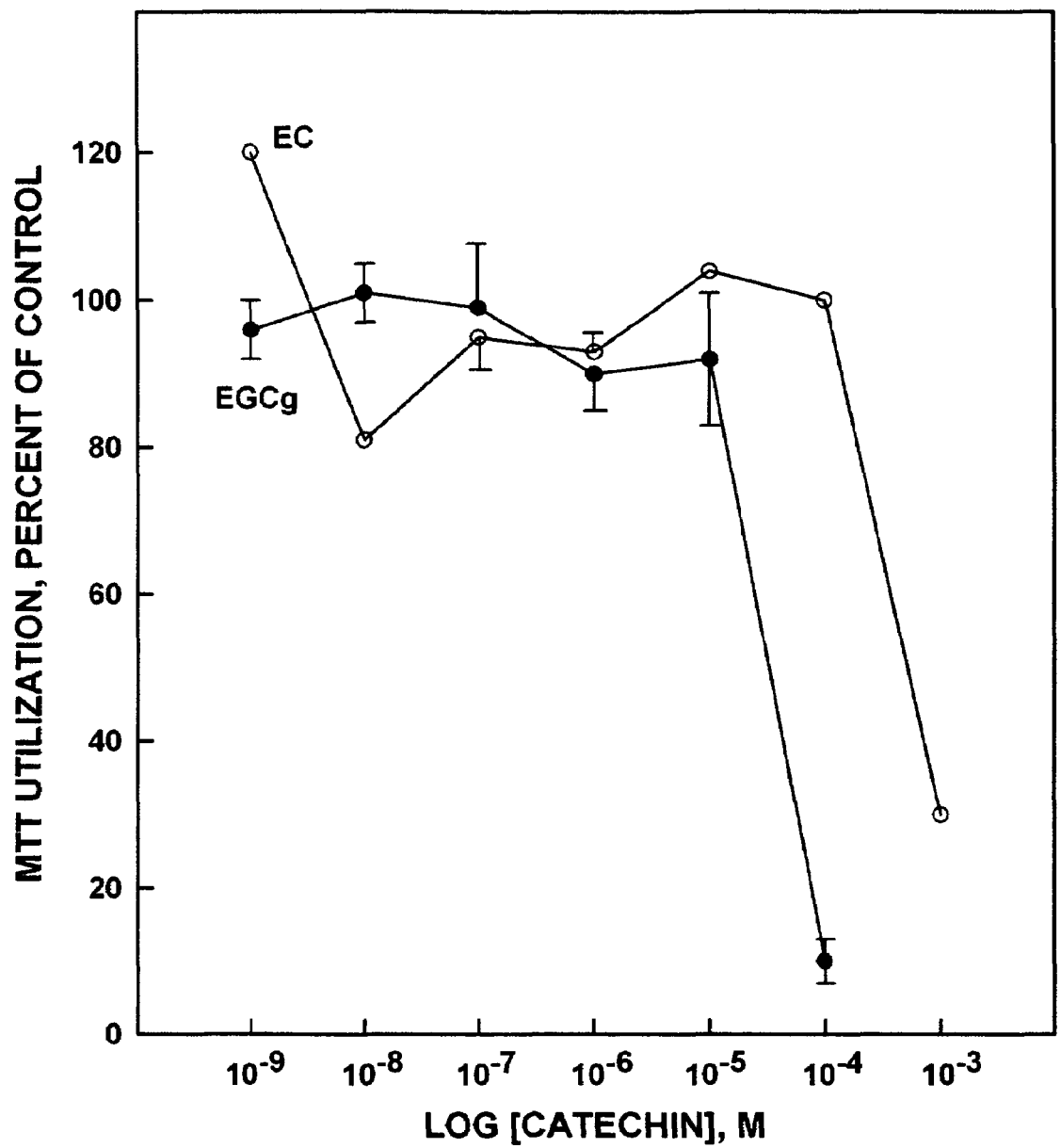
FIG. 3: Toxicity of (−)-epigallocatechin-3-gallate (EGCg) or (−)-epicatechin (EC) to non-infected MT-2 cells assessed by MTT utilization, as described herein below. Average of 3 to 4 independent experiments, each as a fourfold assay. MTT utilization was tested after 4 to 5 d of culture.

There were no cytotoxic effects as measured by MTT utilization at dilutions of less than $10^{-5}$ M of the EGCg. For EC, no toxicity was observed at $10^{-4}$ M but at this concentration, EGCg reduced MTT utilization by 90% (FIG. 3). Yet, since the viability of MT-2 cells was unaffected at concentrations where virus production was lowered, this indicates that the effect of EGCg on virus replication was not due exclusively to unspecific toxicity. Importantly, the EGCg was without effect on the viability of human peripheral blood lymphocytes (data not shown).

Figure 4:
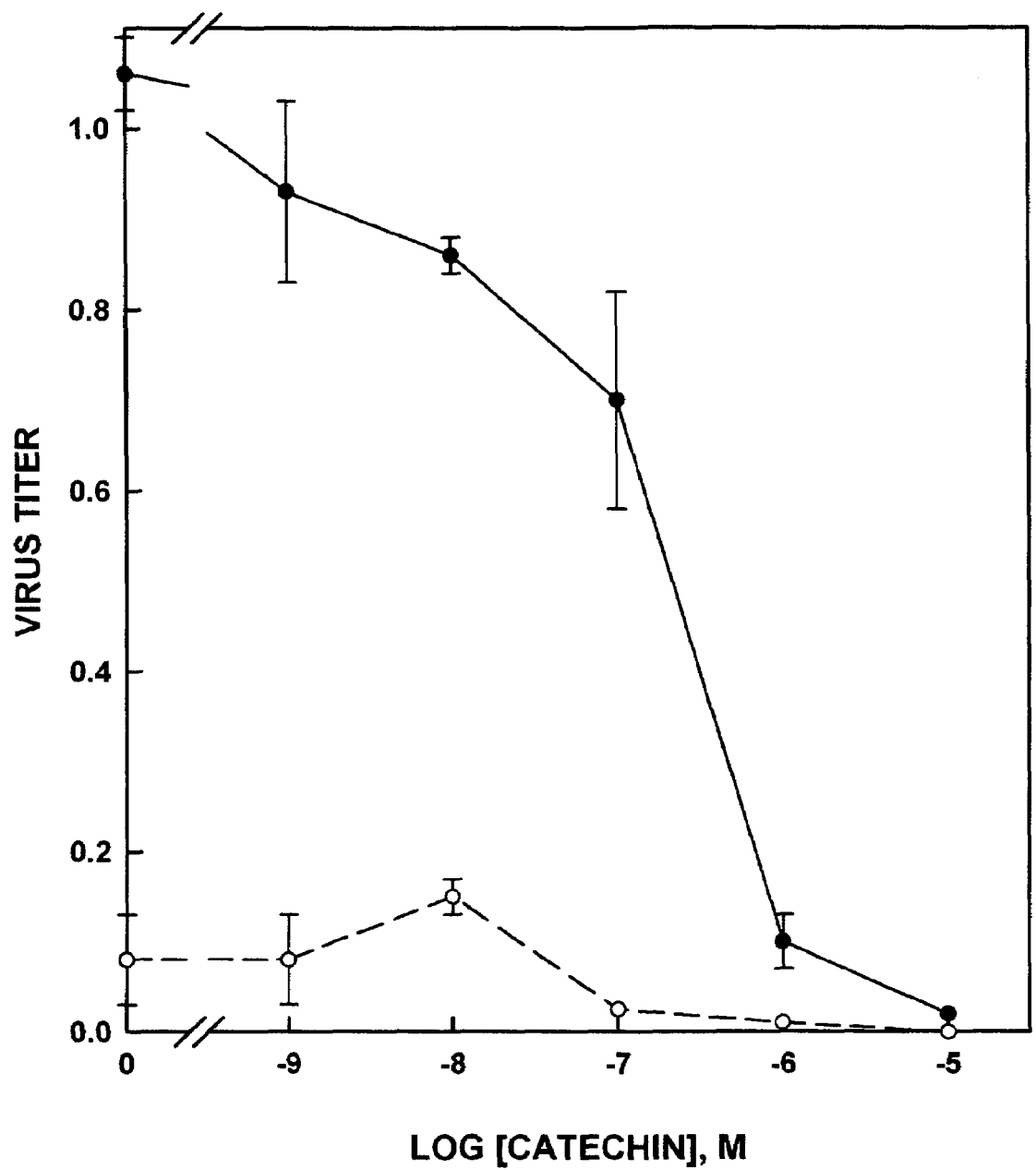
FIG. 4: ELISA of supernatant p24 antigen of HIV-1 strain 952 (solid line; solid symbols) and HIV-1 titer based on number of syncytia observed by light microscopy on day 5 by titration of the day 4 supernatants in previously uninfected MT-2 cells (dashed line; open symbols) as a measure of mature virus production after 4 d with HIV strain 952 (City Laboratory, Hamburg) and mononuclear cells in peripheral blood (PBMCs)=peripheral blood monocytes prepared from healthy volunteers, as described herein below. Assays were in triplicate ±standard deviations.

Using peripheral blood monocytes from healthy volunteers, infection with a local (City Laboratory, Hamburg) strain (952) of HIV, infection (production of infective particles based on p24 assay) was prevented by 10 µM EGCg (FIG. 4). When active virus titer was measured by syncytia formation after 5 days by presenting the PBMC supernatants to uninfected MT-2 cells for assay, the $EC_{50}$ for inhibition of production of infective virus by EGCg was below 1 µM (FIG. 4, lower curve). This response persisted for up to 1 week of culture at which time the experiments were terminated.

Example 2

Figure 5:
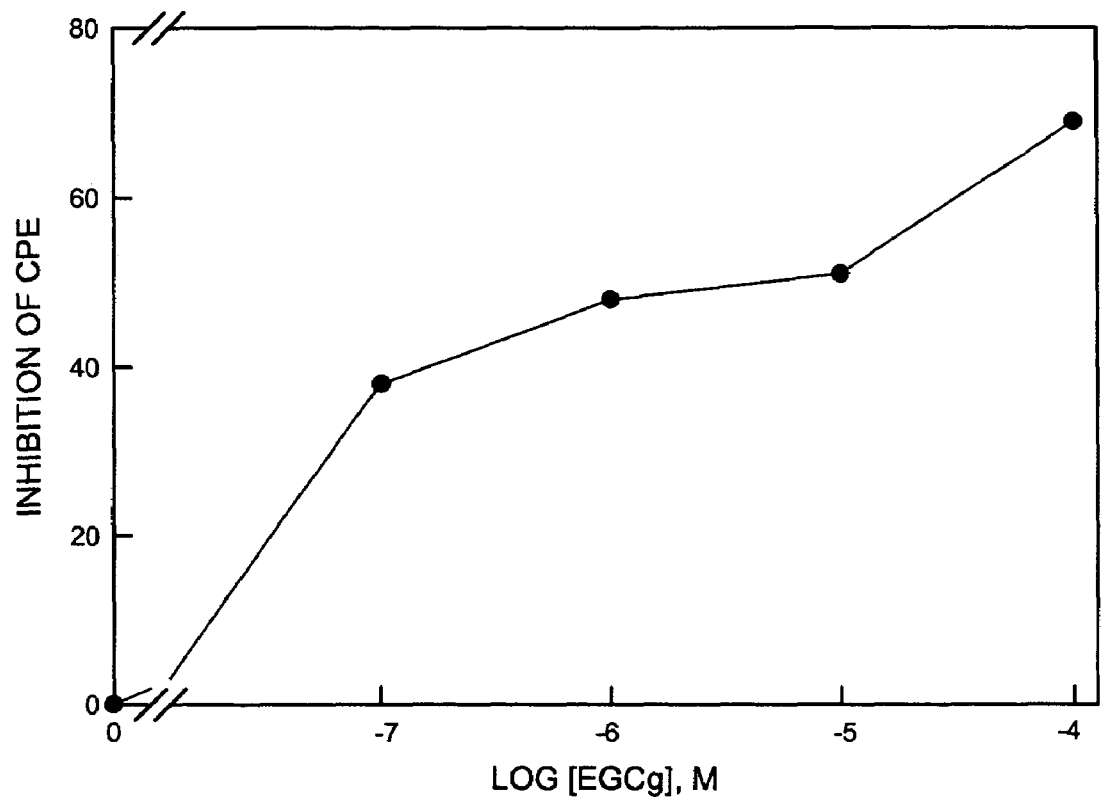
FIG. 5: Dose response of human rhinovirus HRV 14 in HeLa cells (inhibition of CPE) as a function of the logarithm of (−)-epigallocatechin-3-gallate (EGCg) concentration. The $EC_{50}$ was about 1 μM. The XTT test was utilized 72 h post infection.
Figure 6:
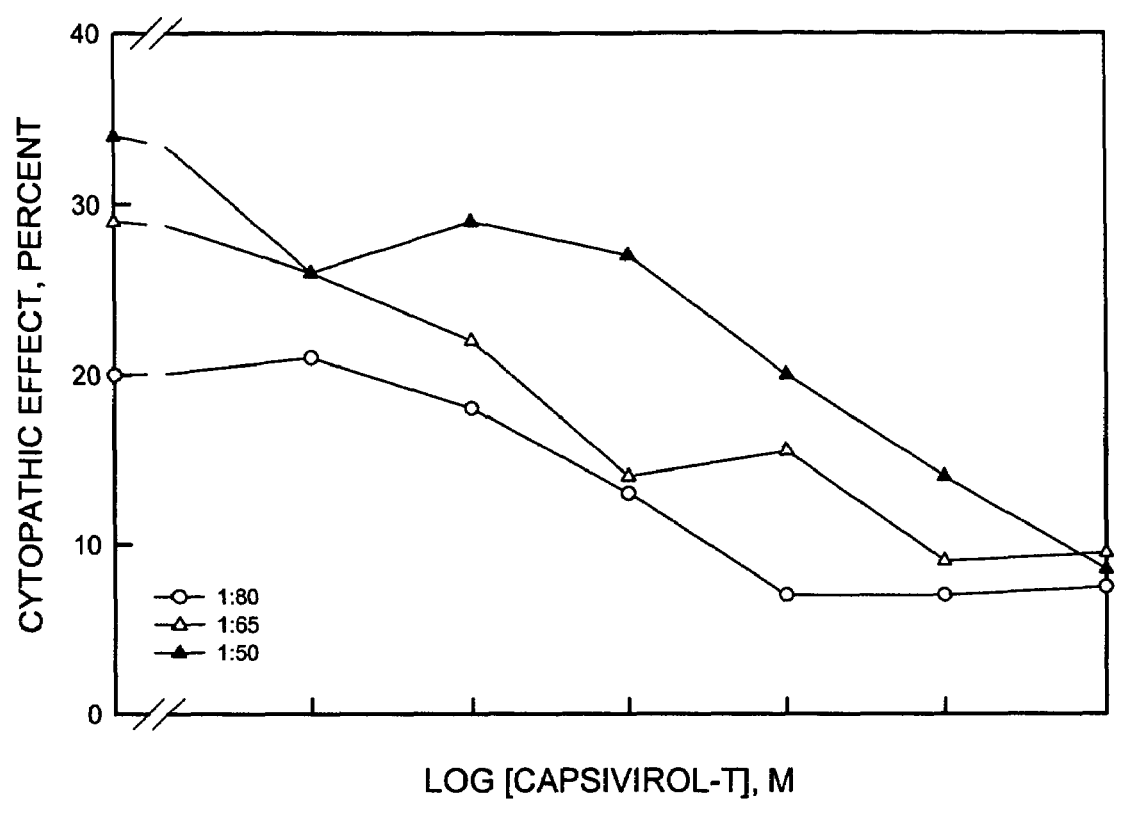
Figure 7:
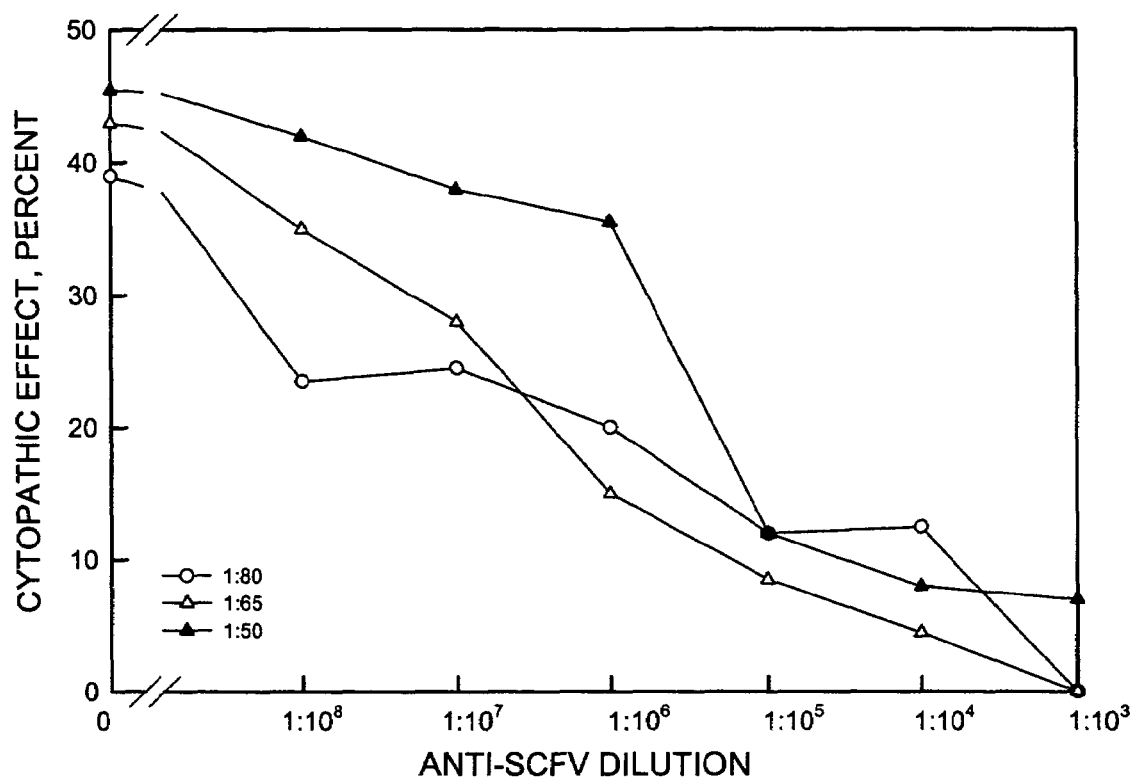
FIG. 7: Dose response of HRV 14 cytopathic effects on Hela cells of recombinant anti-tNOX single-chain variable region antibody (scFv) dilutions (present In media) at three virus titers 72 h after infection. The $EC_{50}$ was determined to be a dilution of 1:170,000.

Non-Prescription Approach to Preventing Common Cold and Reduction in Cold Symptoms Antiviral activity of the compositions of the present invention in a human rhinovirus model system (HRV-HeLa test system) was determined. For virus titration results, see FIGS. 5 and 6. With both Rhinovirus type 14 and Rhinovirus type 16 there was definite evidence for reduced CPE in the presence of CapsiVirol-T. The $EC_{50}$ was in the range of 2 to 50 nM depending on experiment and virus titer. A recombinant anti-tNOX antibody in the media during and after infection also was effective in reducing the cytopathic effect. As for CapsiVirol-T, three virus titers were compared 72 h post infection. The $EC_{50}$ was estimated to be at an antibody dilution of 1:170,000 (FIG. 7).

Pretreatment with CapsiVirol-T did not seem to have much effect (Table I). It was necessary for the product to be present during and/or after virus infection. Surprisingly, there was an apparent response to the CapsiVirol-T added post virus infection. We saw some response into the nanomolar range (as in the past) but prolonged CapsiVirol-T treatment of itself was harmful to the HeLa cells since they are cancer cells and normally express high levels of tNOX. As an alternative to HeLa cells, we sought a non-cancer source of cells that could be infected and assayed for virus presence. Additionally, tests of EGCg and CapsiVirol-T were carried out using a HeLa strain less sensitive to capsaicin and ECGg (obtained from the Free University in Berlin). These results are included below.

Antiviral activity of the compositions of the present invention was determined in test systems as described below.

Figure 8:
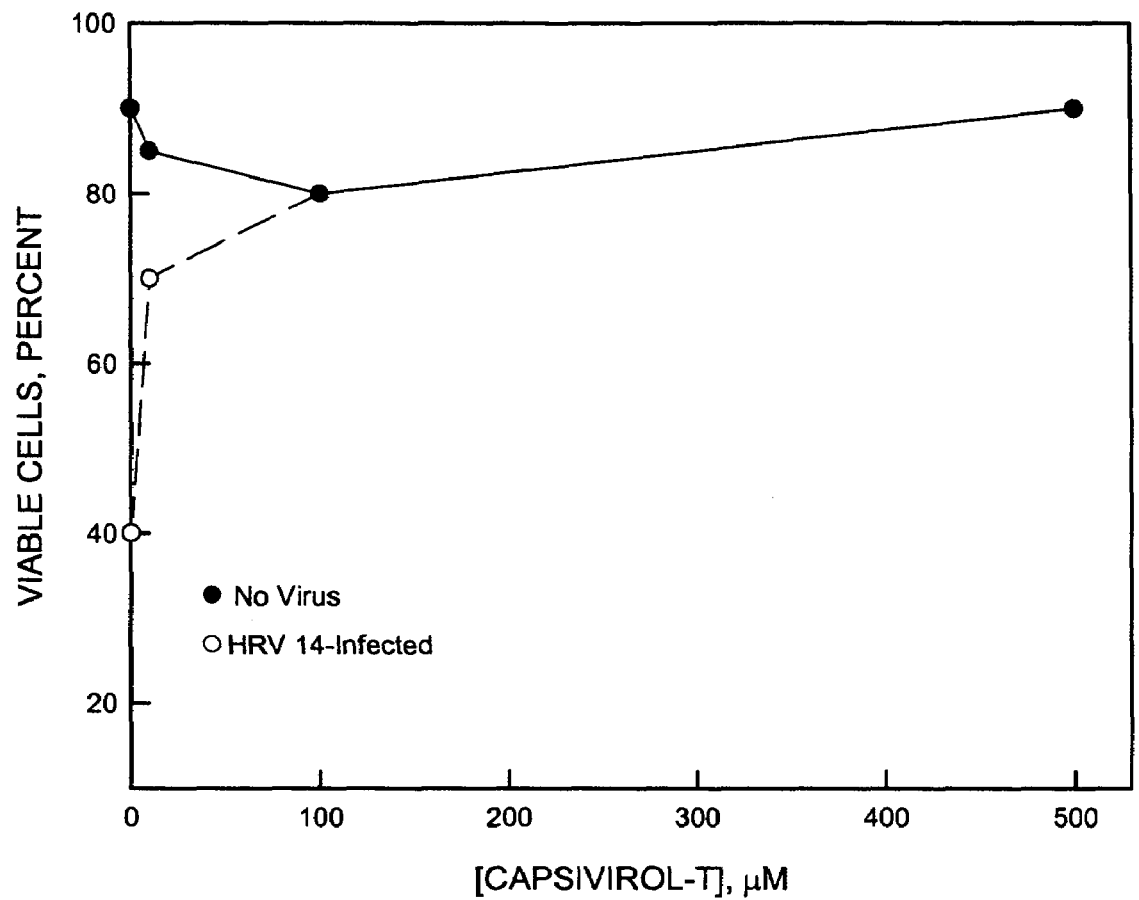
FIG. 8: Rescue of human osteoblast (hFOB) cells from HRV 14-induced cytopathic effect (cell killing) as a function of CapsiVirol-T concentration (10 to 100 μM). Data are 96 h post Infection. The CapsiVirol-T was present during and post virus infection.
Figure 9:
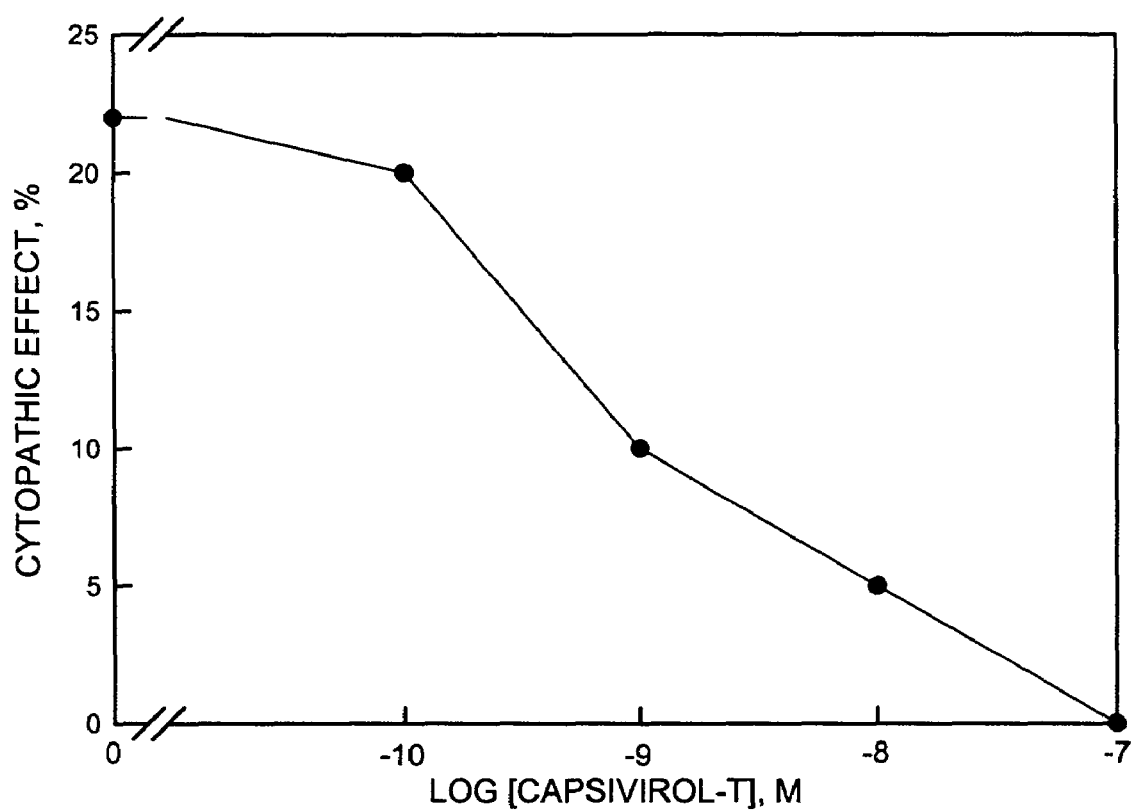
FIG. 9: Dose response to the logarithm of CapsiVirol-T concentration (in the media) of HRV 14 cytopathic effect 72 h after infection for human hFOB cells in culture. The $EC_{50}$ was about 1 nM.
Figure 10:
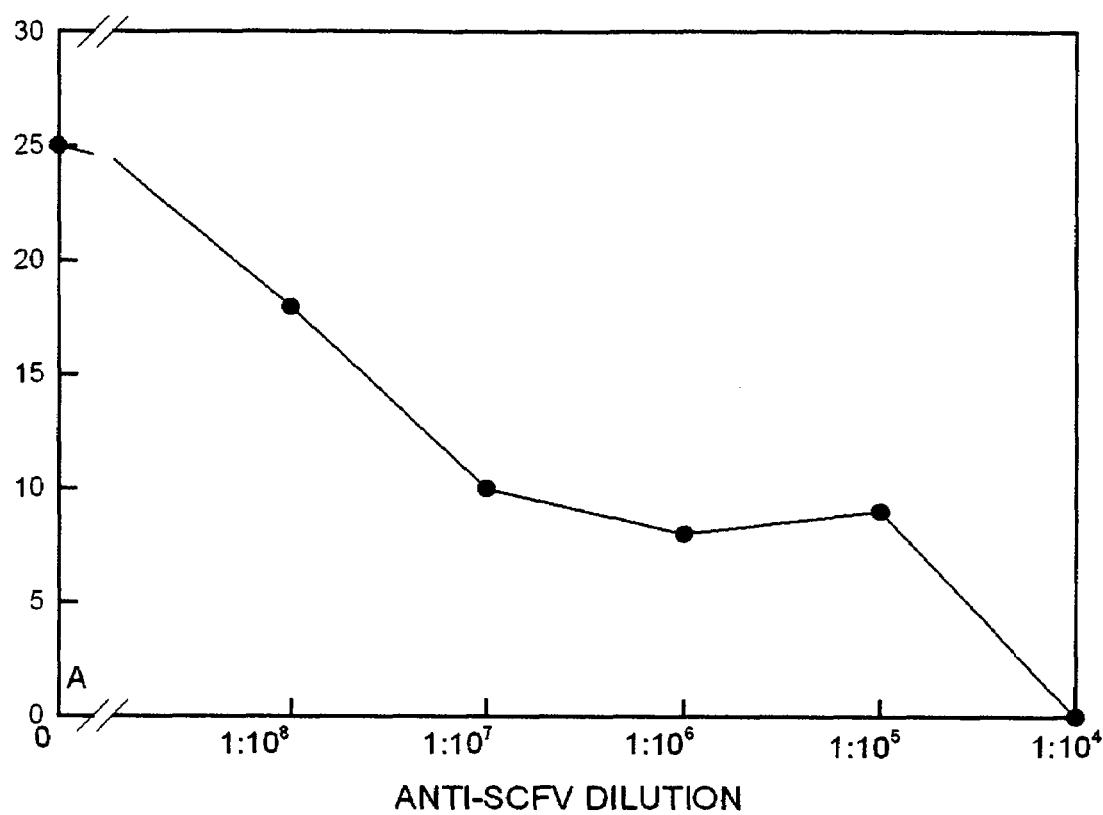
FIG. 10: Dose response anti-tNOX scFv dilution (present In the media) on HRV 14 cytopathic effects on FOB cells 72 h after infection. The $EC_{50}$ was determined to be a dilution of $1:2\times10^7$.

Human osteoblast (hFOB) cells infected with HRV14 showed a cytopathic response that could be prevented by CapsiVirol-T (FIG. 8). On average, the $EC_{50}$ for CapsiVirol-T was 1 nM (FIG. 9) based on analyses at three different virus titers. With the scFv, the cytopathic effect was inhibited completely at a dilution of 1:10,000 (FIG. 10) also based on analyses of three different virus titers. With an $EC_{50}$ in the order of 1:10$^6$, zinc chloride between 1 and 1000 nM reduced the cytopathic effect at a virus dilution of 1:20 by 71±9% and 50%±14% at a virus dilution of 1:50. There was no clear dose response and always some evidence (ca. 10%) of a cytopathic effect at all zinc chloride concentrations tested. While potentially useful, the hFOB osteoblast model was insufficiently robust to have extensive utility. A maximum cytopathic effect of 40% was one limitation (Table II). Also, the hFOB cells were unstable and needed to be reisolated after only a few passages.

WI-38 human epithelia were investigated but showed a poor cytopathic effect. These cells also grew very slowly and stopped growing actively after several passages as is commonly observed with this cell line.

The non-cancer MCF-10A human mammary epithelial cell line, while failing to generate a significant cytopathic effect, could be infected with a human rhinovirus (HRV14) and provides a useful source of target protein for biochemical assay.

Figure 11:
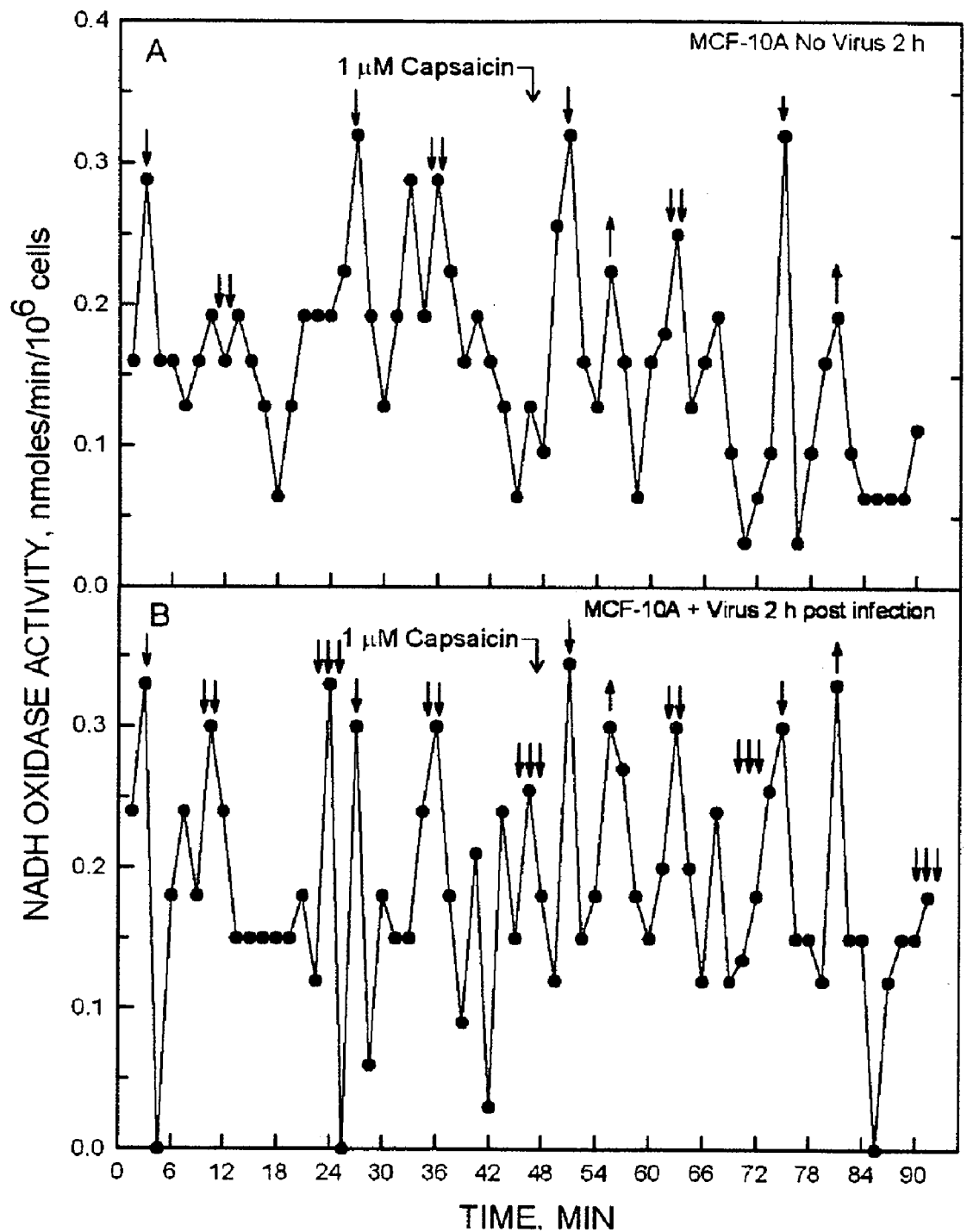
FIG. 11: NADH oxidase activity assayed for 90 min at the surface of MCF-10A human mammary epithelial cells. Capsaicin (1 μM) was added after 45 min and the assay was continued for an additional 45 min. Top Panel: No virus. Bottom Panel: MCF-10A human mammary cells infected with HRV 14. The MCF-10A cells normally lack a drug-inhibited NOX activity (lack tNOX). The normal, capsaicin-resistant constitutive NOX activity with a period length of 24 min is shown by the single downward pointing arrows. The triple arrows are tNOX-like activities with a period length of 22 min and which were inhibited by capsaicin. This activity appeared only in the virus-infected cells (see also FIG. 12). The upward pointing arrows denote a capsaicin-stimulated activity sometimes observed in proliferating endothelial cells present both with and without virus. tNOX-like activities (triple arrows) inhibited by 1 μM capsaicin now dominate the activity pattern.
Figure 12:
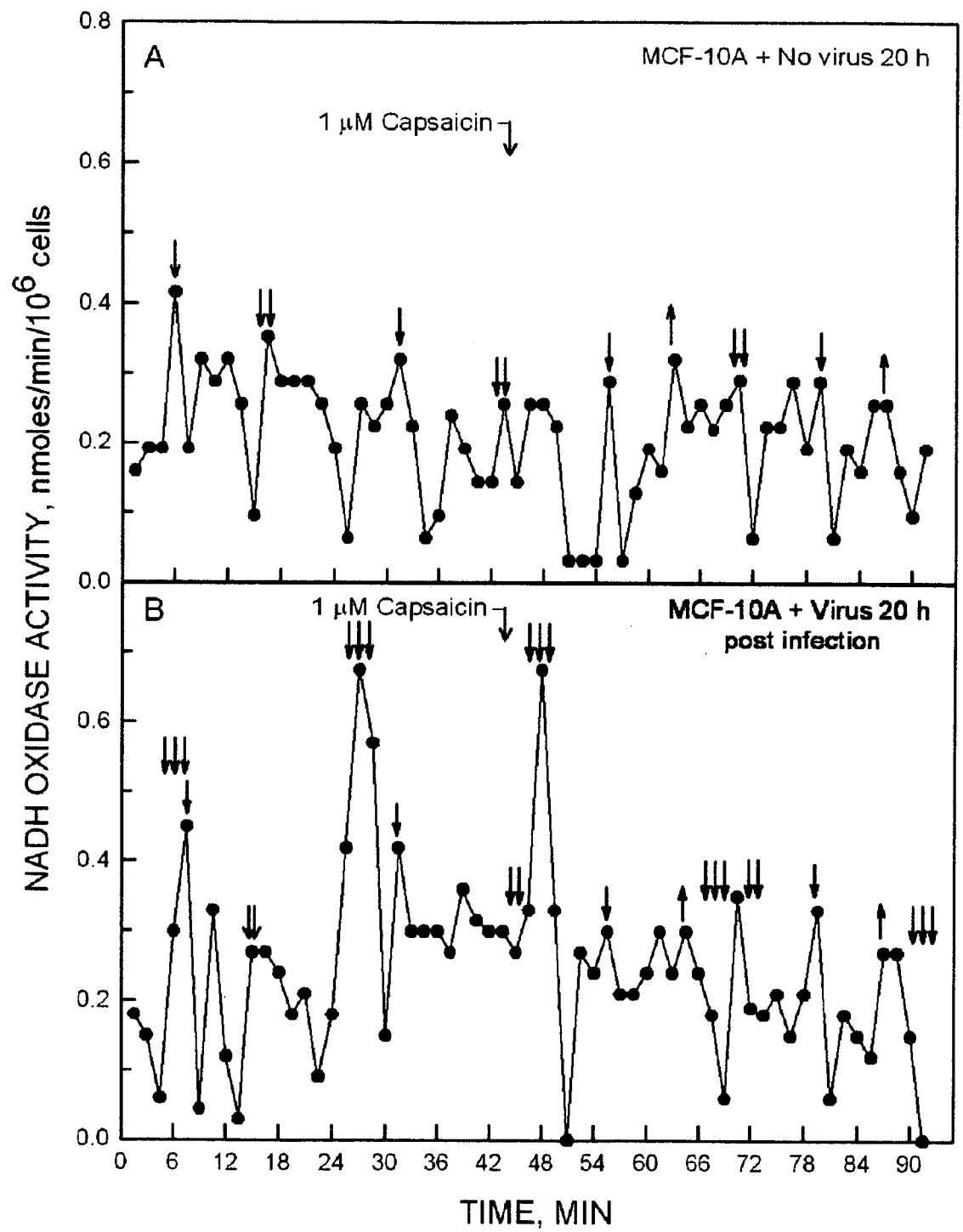
FIG. 12: As in FIG. 11 except 20 h post-infection with HRV 14. Top Panel: No virus. The control MCF-10A cells normally lack a drug-inhibited NOX activity (lack tNOX). Bottom Panel: MCF-10A cells 20 h post infection with HRV 14. The normal, capsaicin-resistant constitutive NOX activity with a period length of 24 min is shown by the single downward pointing arrows. The triple arrows are tNOX-like activities with a period length of 22 min and which were inhibited by capsaicin. This activity appeared only in the virus-infected cells (see also FIG. 11). The upward pointing arrows denote a capsaicin-stimulated activity sometimes observed in proliferating endothelial cells present both with and without virus. tNOX-like activities (triple arrows) inhibited by 1 μM capsaicin now dominate the activity pattern.

HRV14 infection induces a tNOX-like activity in MCF-10A non-cancer mammary epithelia. For these studies, human mammary epithelial cells (MCF-10A cells) which completely lack tNOX were infected with HRV type 14 and examined 2 and 20 h post infection for ECTO-NOX activity. Both after 2 h and more markedly 20 h post infection, a NOX activity with a period length of ca. 22 min that was inhibited by CapsiVirol-T was observed (FIGS. 11 and 12). This substantiated what we observed earlier with feline immunodeficiency virus as the basis for the HIV and HRV work using tNOX-directed inhibitors.

Figure 13:
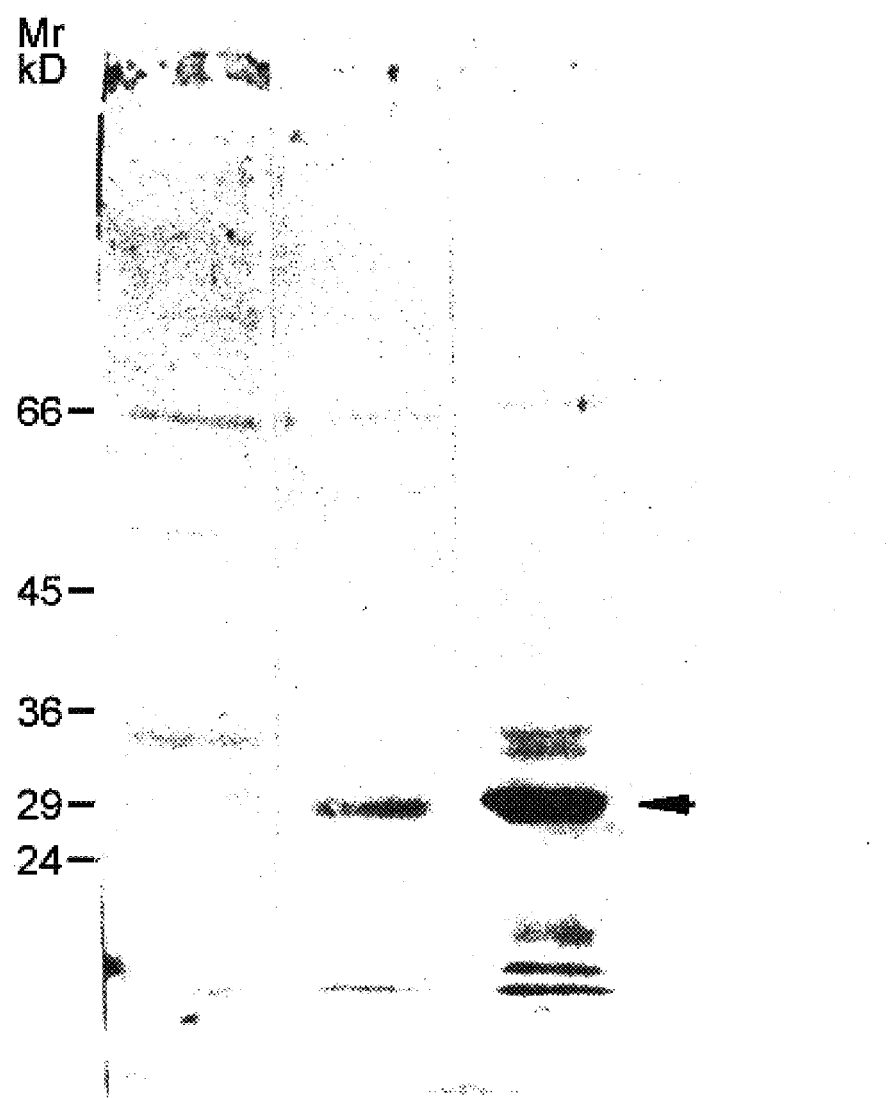
FIG. 13: Western blots of SDS-PAGE (10% gels) of MCF-10A (non-cancer mammary epithelia) cells uninfected (left lane) or infected after 3 h or 24 h (right two lanes) with HRV 14. A band at 29 kD (arrow) absent from uninfected cells (left lane) appears rapidly post HRV 14 infection (right two lanes) and increases with time together with several additional bands at later time points. Detection was with an antibody to the conserved C-terminal adenine nucleotide binding region of tNOX (peptide antibody). The experiment has been repeated both with human rhinovirus type 14 (20 h) and human rhinovirus type 16 (24 h).

The presence of a novel ECTO-NOX form induced in HRV-infected MCF-10A cells (vNOX) was demonstrated unequivocally. In these cells, which totally lack tNOX, HRV infection resulted in a very rapid and massive induction of a functional tNOX-like protein. This was shown by measurement of enzymatic activity (FIGS. 11 and 12), Western blot analysis using tNOX specific antibodies (FIG. 13), and Immunocytochemistry (FIG. 14). Not only is the tNOX-like determinant produced (induced) upon HRV infection, but the vNOX protein appears to be delivered to the cell surface as well, as predicted from earlier studies.

The virus induction of a characteristic tNOX-like protein is not restricted to RV but is also observed with two virus vectors used for transfections. The induction of vNOX by the virus vectors explains some previously troubling animal data where MCF-10A cells transfected with virus vector alone proliferated at a much greater rate than did MCF-10A cells alone (no proliferation) in immunocompromised mice. We also have observed a tNOX-like activity in 3T3 cells following infection by SV40 virus, but the time course is much slower than that observed with HRV and MCF-10A cells.

Figure 15:
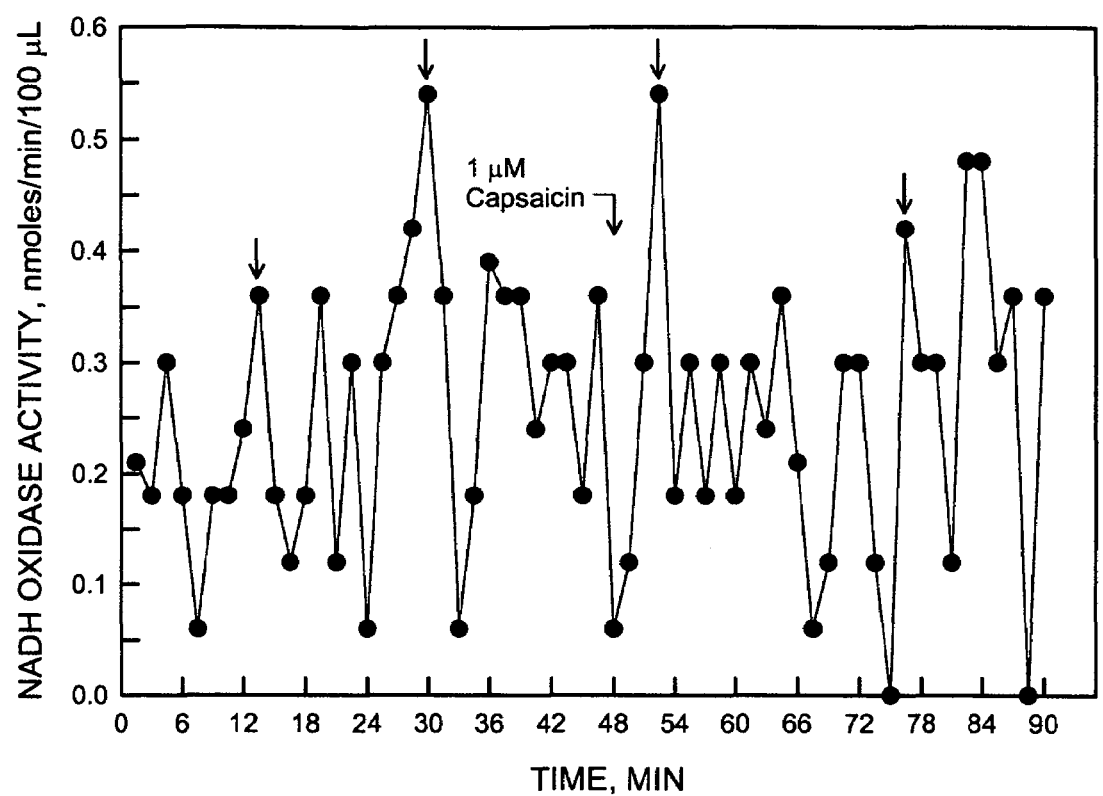
FIG. 15: NADH oxidase activity of culture media 96 h post infection of MCF-10A cells infected with HRV 14. The supernatants contained only the constitutive (CNOX) activity with a period length of 24 min (single arrows). The assay was initiated at t=0. Capsaicin (1 μM) was added after 45 min and the assay was continued for an additional 45 min.
Figure 16:
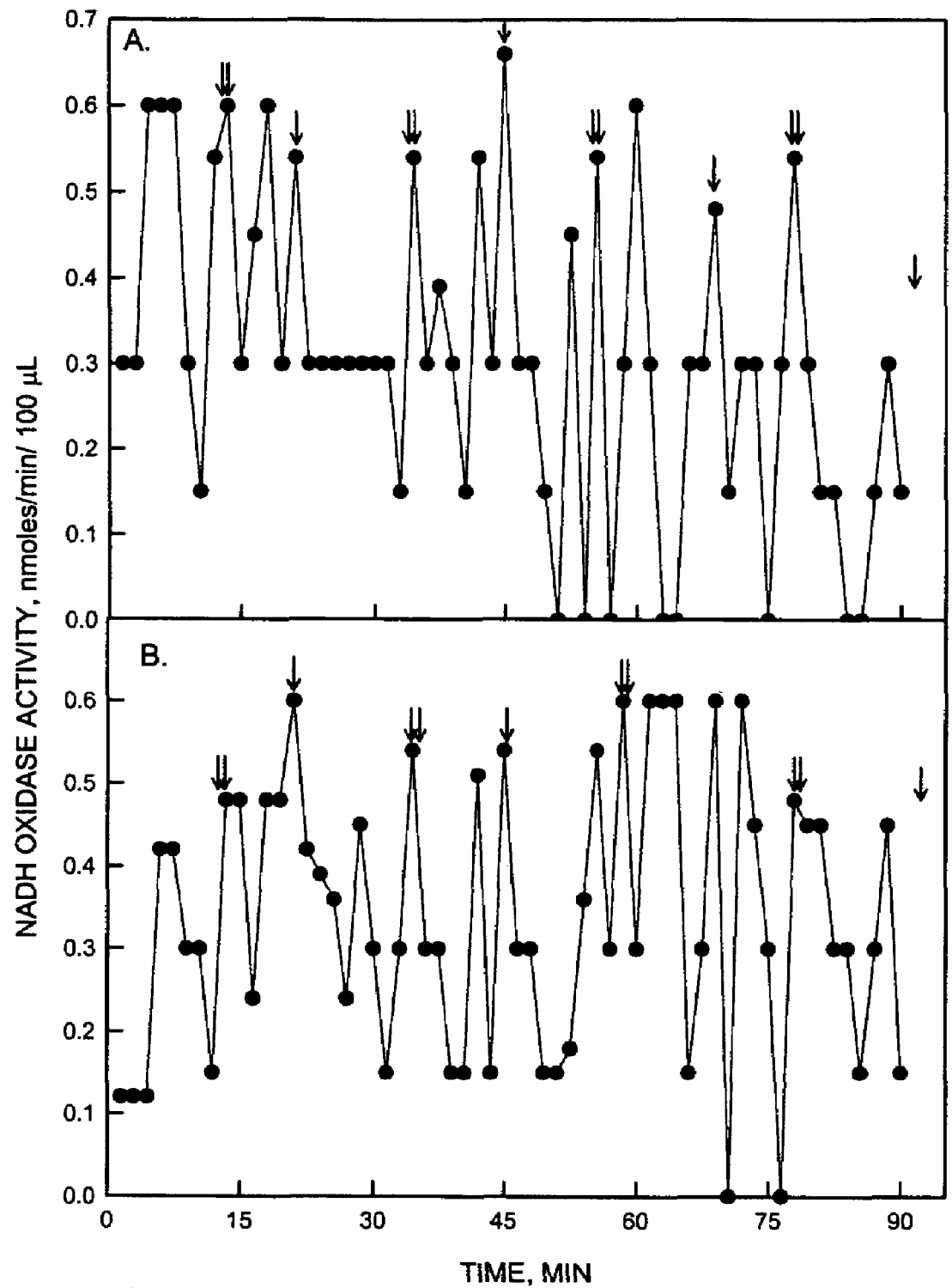
FIG. 16: NADH oxidase activity of culture media 96 h post infection comparing non-infected (lower panel) and HRV 14-infected (upper panel) HeLa cells. The HeLa cells (human cervical carcinoma) release both the constitutive (CNOX) activity with a period length of 24 min (single arrows) and a capsaicin-inhibited tNOX with a period length of 22 min (double arrows). The two activity patterns determined in parallel with two different spectrophotometers were virtually indistinguishable suggesting that, even with HeLa cells, the virus-induced tNOX-like activity is not shed into the culture medium. This characteristic, along with a very different processed molecular weight, distinguished the viral NOX (vNOX) from the cancer-associated NOX (tNOX).

In addition to a distinctive molecular weight of 29 kDa (compared to 34 kDa for tNOX) (FIG. 13), the viral tNOX-like activity (vNOX) apparently is not shed from the cell surface, unlike tNOX. Assays of culture medium from virus-infected MCF-10A cells which lack tNOX show no presence of a tNOX-like activity. Only CNOX, with a period length of 24 min, is found (FIG. 15). In contrast, HeLa (human cervical carcinoma) cells which express tNOX shed both CNOX and tNOX (FIG. 16B) but the activity pattern is unaffected by virus infection (FIG. 16), again suggesting that vNOX differs from tNOX by not being shed. These findings were confirmed by Western blot analyses.

Figure 17:
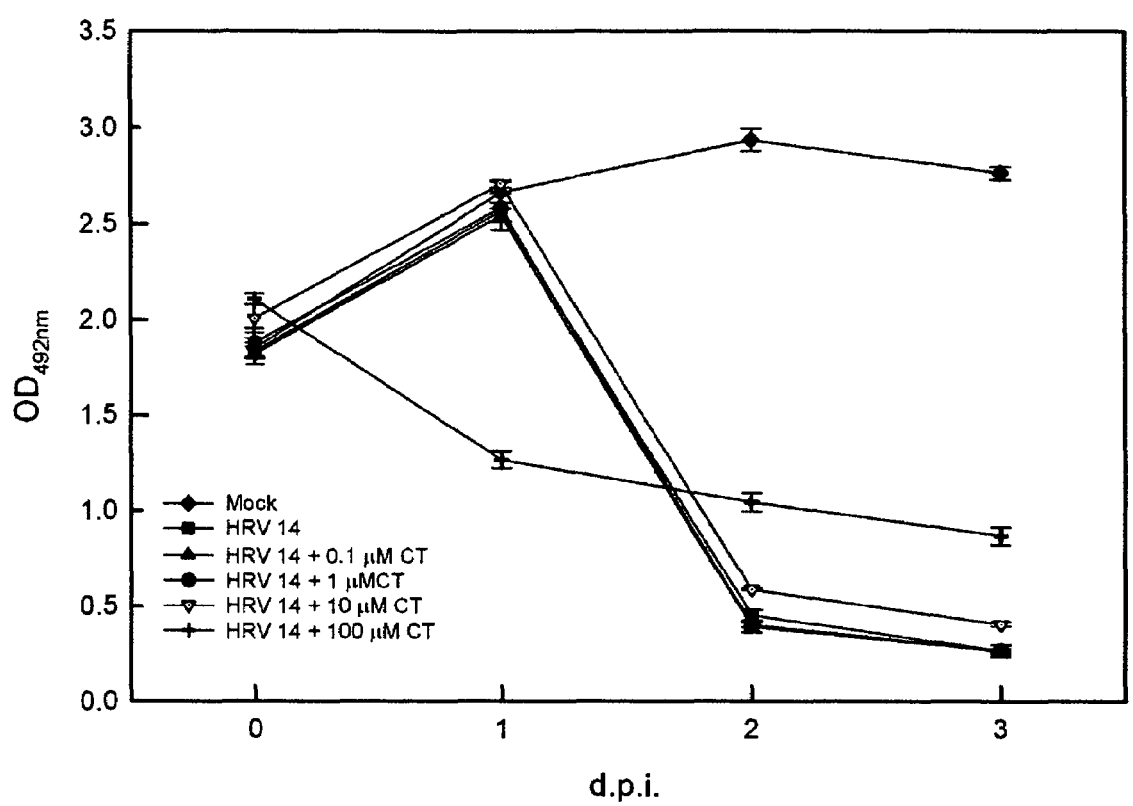
FIG. 17: Inhibition of HRV 14-induced CPE in HeLa cells (0.1 m.o.i.) by 0.1 to 100 μM CapsiVirol-T (CT), XTT test.

Inhibition by CapsiVirol-T of the HRV cytopathic effect and effects on cell viability were tested using a HeLa strain which is less sensitive to tNOX inhibitors than certain other HeLa cells (Institute for Infectious Medicine, Berlin, Germany) (FIG. 17). In these studies, both CapsiVirol-T and EGCg, the principal green tea catechin, were tested. Monolayers of HeLa cells (in Eagle's MEM with 5% FCS) in 96 well tissue culture plates were pretreated with the test substance for 1 h before the infection. The test substance-containing medium was removed and the cells were infected with viruses at a multiplicity of infection of 0.1. For controls, virus infections were in the absence of the test substance. Mock infections were in the presence and absence of the test substance.

Cell viability was measured in the XTT test directly at the days post infection (d.p.i.) indicated (FIG. 17). The XTT test measures the conversion of the XTT dye (soldium-3'-[1-(phenylamino-carbonyl)-3,4-tetrazolium]-bis (4-methoxy-6-nitro) benzenesulfonic acid) in a colorimetric test (absorbance measured at 492 nm) as a measure of mitochondrial dehydrogenase. The cytopathic effect induced by a virus was determined from a decrease of cell viability (=decrease of $A_{492}$ nm in comparison to the mock infected control in the absence of the test substance).

For studies with CapsiVirol-T, the HeLa cells were preincubated with the CapsiVirol-T for 60 min and then infected with HRV14 (at a multiplicity of infection (m.o.i.) of 0.1.). Cell viability was measured with the XTT test. Virus inoculation in the presence of CapsiVirol-T (without FCS) was for 30 min. After the inoculum was removed, Eagle's MEM medium with CapsiVirol-T present (with 5% FCS) was added according to the concentrations (0.1, 1, 10 and 100 µM) specified for FIG. 17.

Figure 18:
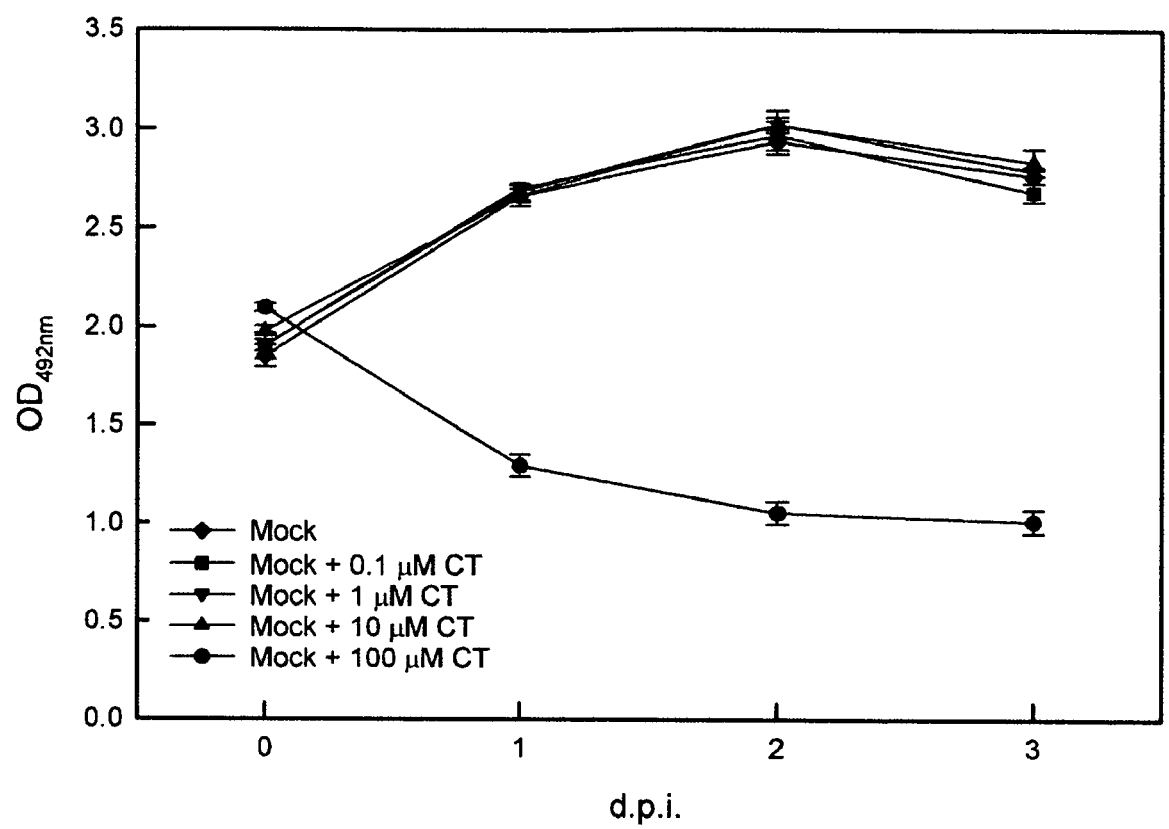
FIG. 18: Inhibition of cell viability in mock-infected HeLa cells by 0.1 to 100 μM CapsiVirol-T (=toxicity), XTT test.

Cell viability was monitored using the XTT test after 1, 2, and 3 days p.i. A control was at 1.5 h p.i. (in the figure 0 d p.i.) (FIG. 18). High OD values represent living cells, and low OD values represent cell damage. This damage is either induced by HRV14 (=cytopathic effect/CPE) or a toxic effect of the compound in mock-infected cells.

With CapsiVirol-T concentrations of 0.1 µM, 1.0 µM, 10 µM and 100 µM were examined. CapsiVirol-T concentrations up to 10 µM did not show any significant inhibition of HRV14 induced CPE (FIG. 17). At 100 µM CapsiVirol-T, the inhibitory effect overlapped by strong toxicity (FIG. 18), was seen.

Figure 19:
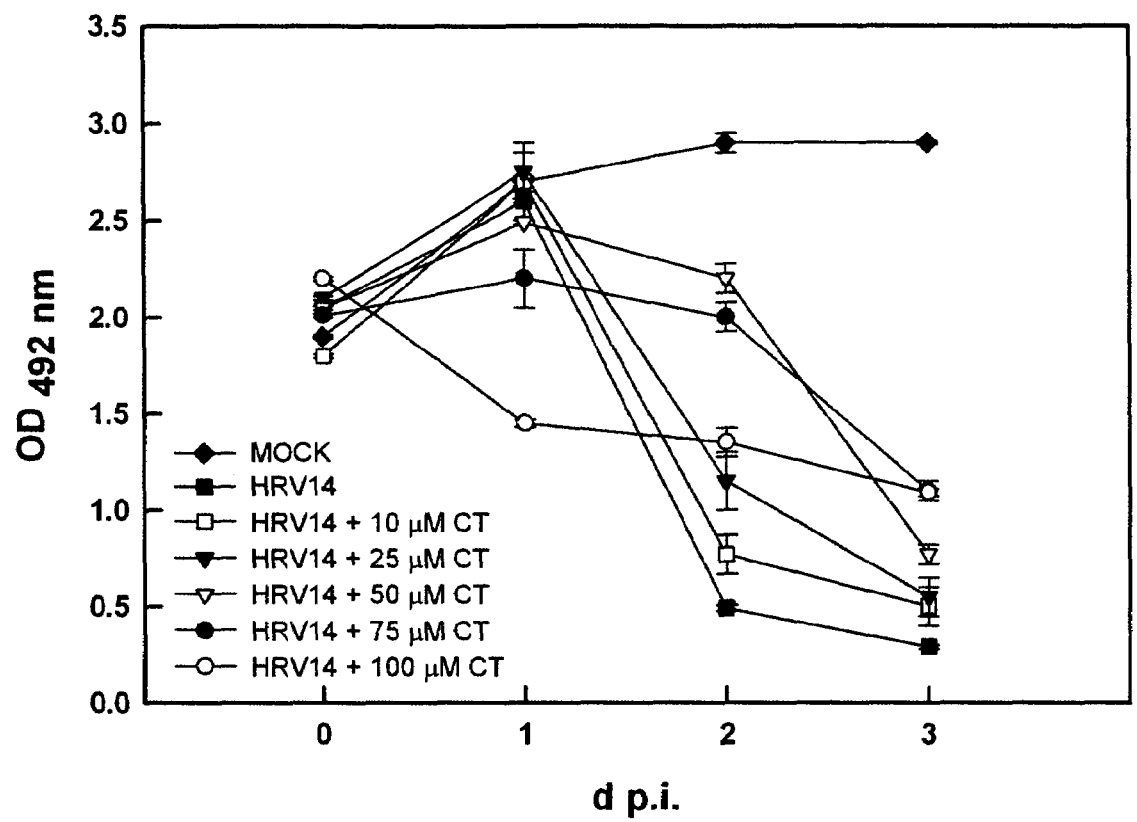
FIG. 19: Inhibition of HRV 14-induced CPE in HeLa cells by 10 to 100 μM CapsiVirol-T (CT), XTT test.
Figure 20:
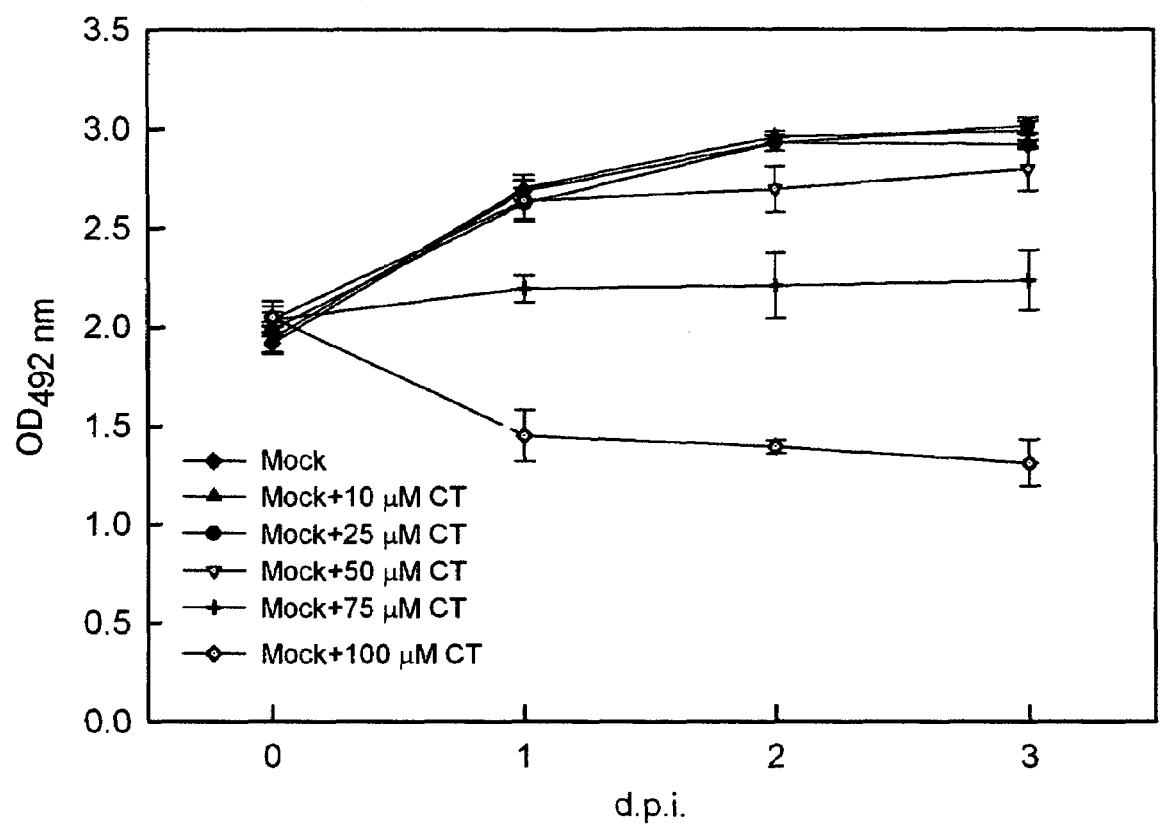
FIG. 20: Inhibition of cell viability in mock-infected HeLa cells by 10 to 100 μM CapsiVirol-T (=toxicity), XTT test.

When we used narrow concentration intervals from 10 µM to 100 µM CapsiVirol-T, a pronounced inhibitory effect on HRV14 (−69%) became discernable at 50 µM CapsiVirol-T (FIG. 19). The toxicity was only −8% at this concentration (FIG. 20).

Figure 22:
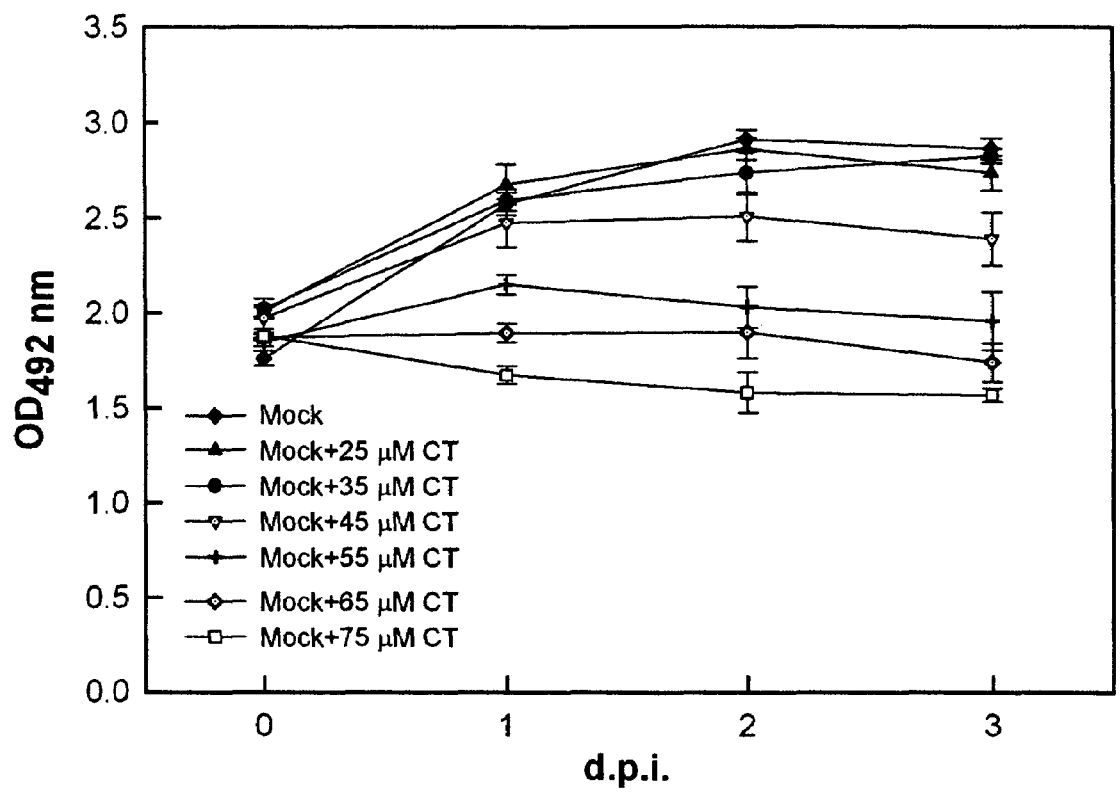
FIG. 22: Toxicity of 25 to 75 μM CapsiVirol-T (CT) in mock-infected HeLa cells, XTT test.

In a third series of experiments with the Berlin strain of HeLa cells, the CapsiVirol-T concentration interval was narrowed down to 25, 35, 45, 55, 65 and 75 µM. The $EC_{50}$ was achieved approximately at 35 µM (−58% inhibition). The toxicity was only −6% at 35 µM, but significantly increased with higher concentration (FIG. 22).

Figure 23:
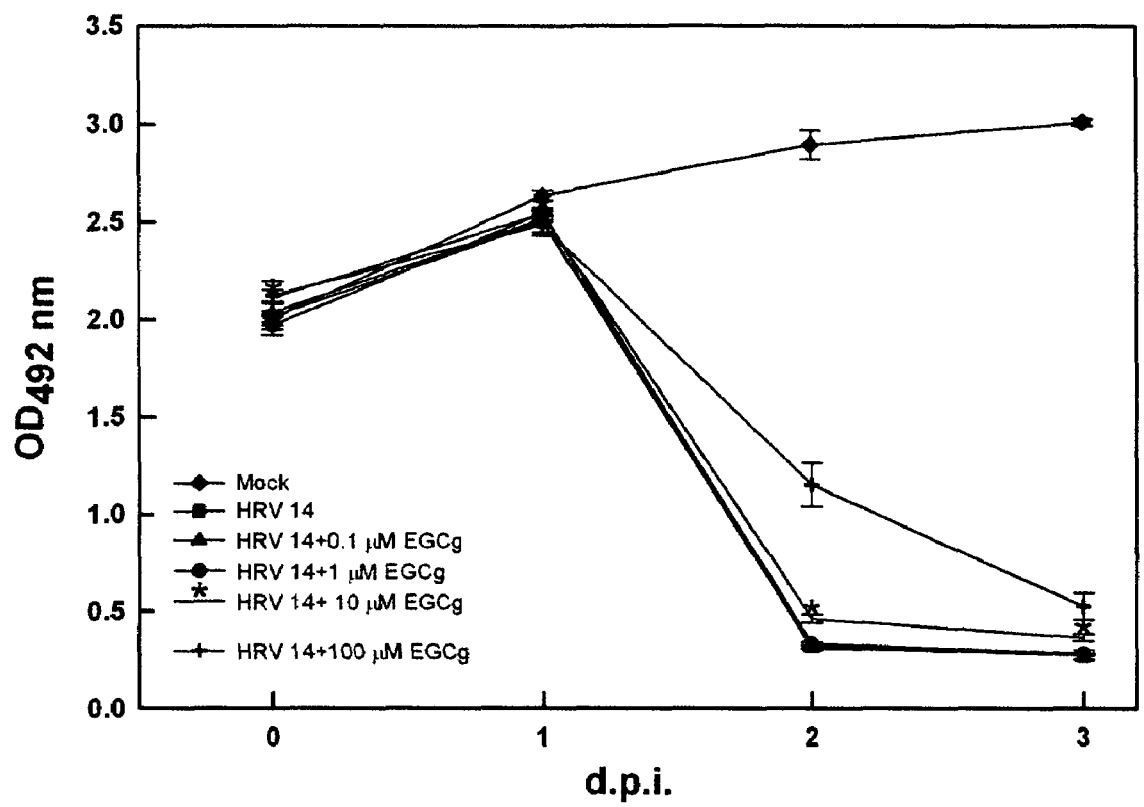
FIG. 23: Inhibition of human rhinovirus 14 (HRV-14)-induced CPE in HeLa cells by 0.1 to 100 μM EGCg, XTT test.
Figure 24:
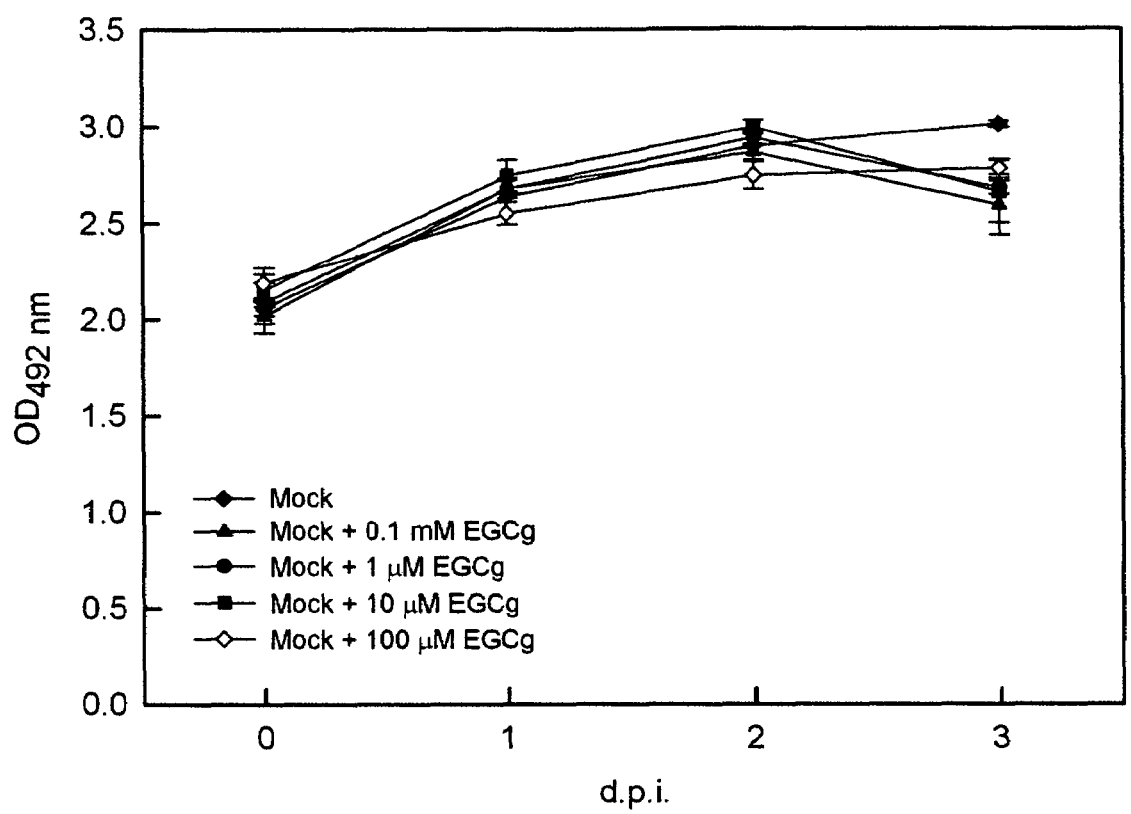
FIG. 24: Inhibition of cell viability in mock-infected HeLa cells by 0.1 to 100 μM EGCg; d.p.i., days post (mock) infection, XTT test.

With EGCg alone at least a 10-fold higher concentration compared to CapsiVirol-T was required to achieve inhibition and the inhibition was less complete (FIG. 23). For EGCg, the EC50 on day 1 to prevent a cytopathic effect was <0.1 µM and 0.1 µM on day 2. EGCg was not toxic at these concentrations (FIG. 24).

Example 3

HRV-induced vNOX of MCF-10A Cells and Response to Putative Cold Preventatives

A rapid and reproducible assay system directed to the vNOX target was developed that allows for direct comparison of the efficacy of health care products in blocking the activity and to facilitate comparisons needed for the eventual development of an OTC anti-colds product. The assay used virus-infected (72 h) MCF-10A cells and a quantitative spectrophotometric approach specific, in this case, for vNOX. In a concentrated GSH redox buffer, apparently only the vNOX at the surface of the cells remained active. Non-infected cells lacked the activity and the level of activity correlated with the HRV-specific 29 kDa band. The rate of oxidation of NADH determined in duplicate over 5 min with uninfected cells as a blank or specificity control was the endpoint selected.

Figure 21:
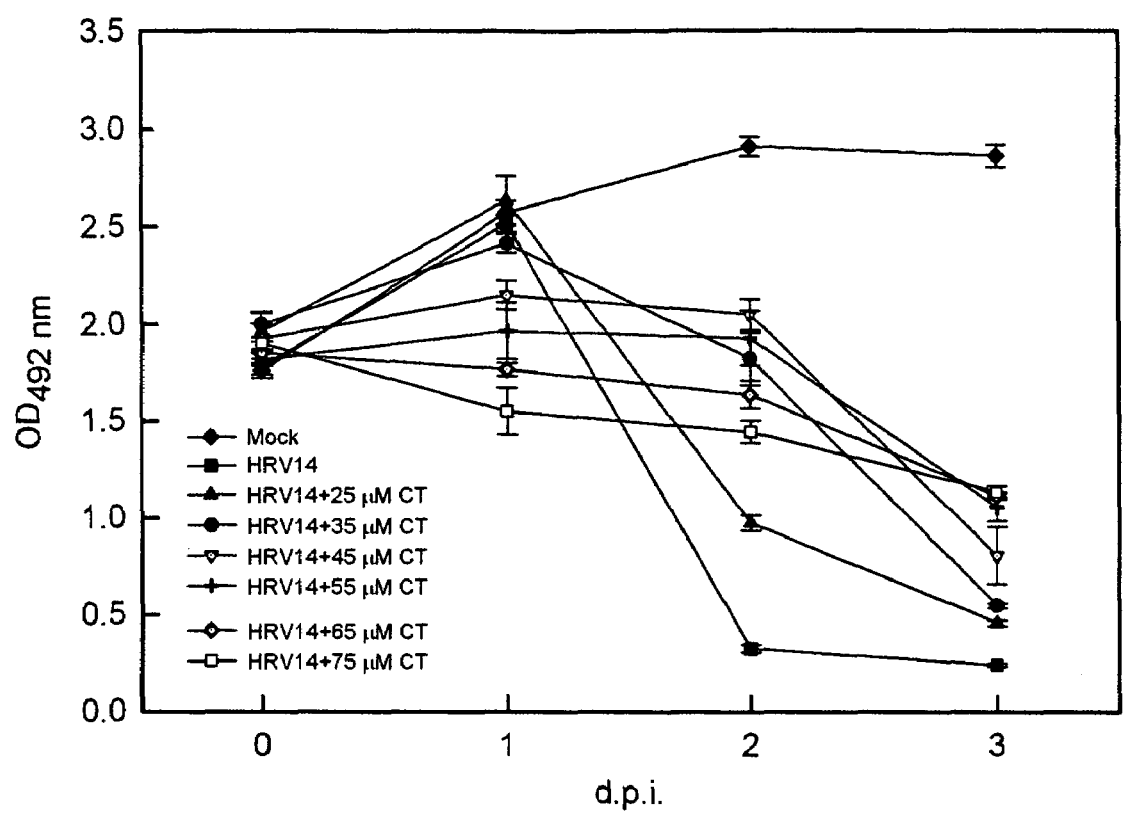
FIG. 21: Inhibition of cell viability in mock-infected HeLa cells and in HRV 14-infected cells (0.1 m.o.i.) by 25 to 75 μM CapsiVirol-T (=toxicity), XTT test.

The dose response for CapsiVirol-T show an $EC_{50}$ of inhibition at a dilution of ca 1:10,000 (equivalent to an EGCg concentration of approximately 10 nM) (FIG. 21). Inhibition is complete at a dilution of 1:100 (equivalent to an EGCg concentration of 1 µM). There was no response over this range of concentrations when the infected cells were replaced by uninfected cells in the assay. The assay is surprisingly reproducible. A number of the compounds were tested with two different productions of infected MCF-10A cells with similar results.

For initial validation of the assay, comparisons were with ablation of the cytopathic effect of the virus in infected HeLa cells. Shown are two figures, one for CapsiVirol-T (FIG. 6) and one for the anti-tNOX scFv (FIG. 7), each at three virus titers. On average, the $EC_{50}$ for CapsiVirol T in this experiment was 20 nM (the range for the cytopathic effect was 2 to 50 nM) which compared very favorably to the $EC_{50}$ of 10 nM for inhibition of the vNOX.

Figure 26:
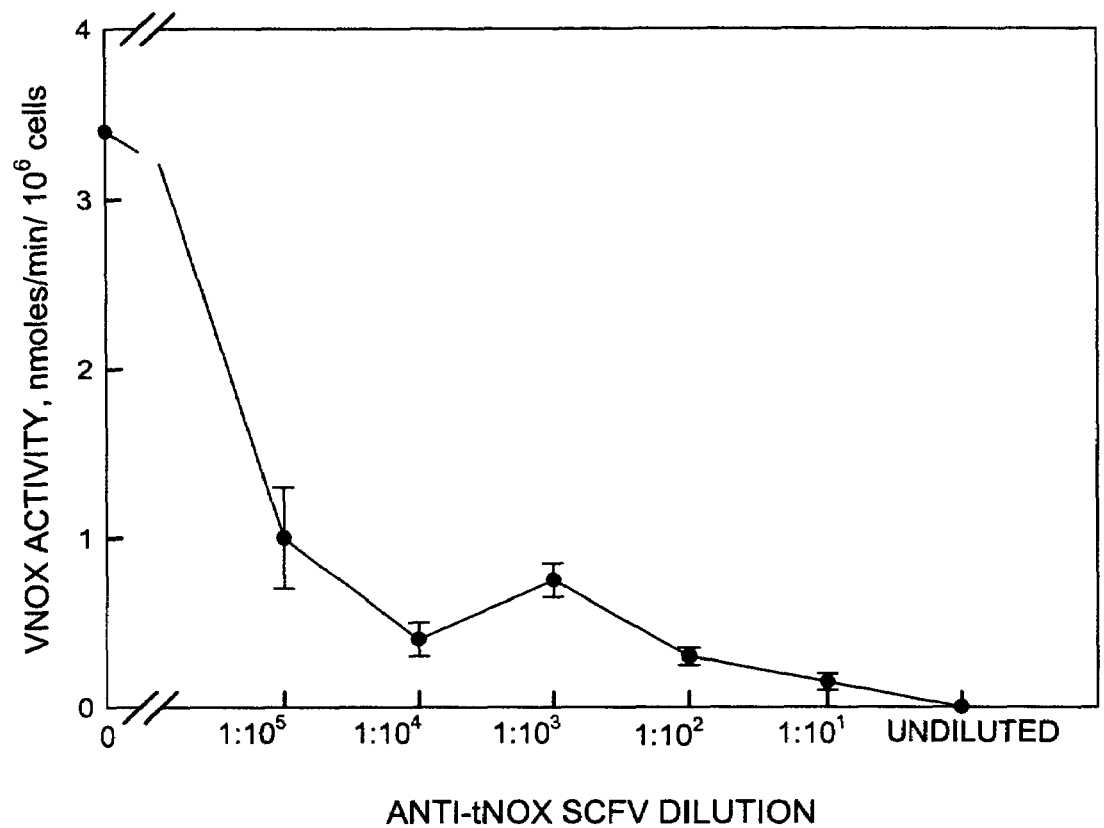
FIG. 26: Inhibition of HRV 14-induced vNOX activity of infected (72 h) MCF-10A cells as a function of scFv dilution (see FIG. 7). The $EC_{50}$ is at a dilution of 1:170,000.
Figure 28:
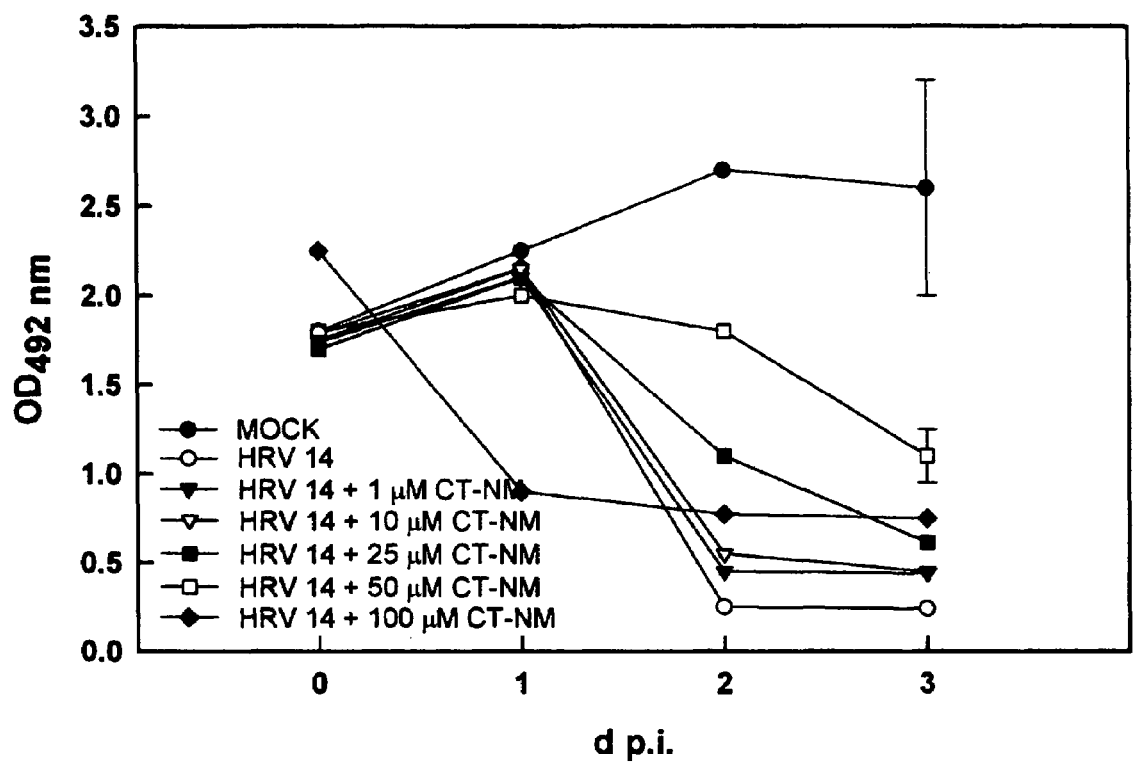
FIG. 28: Inhibition of human rhinovirus 14 (HRV14) induced CPE in HeLa cells by 1 to 100 μM CapsiVirol-T NM, XTT test.
Figure 29:
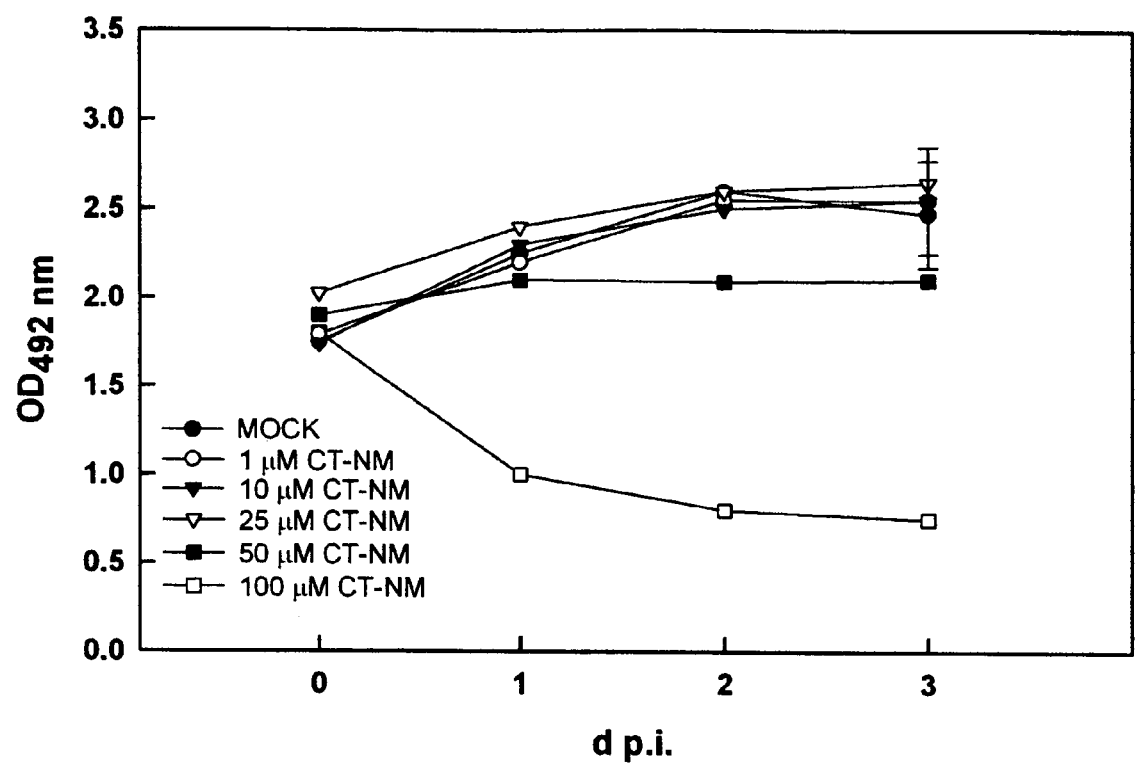
FIG. 29: Toxicity of CapsiVirol-T NM in HeLa cells, XTT test.
Figure 30:
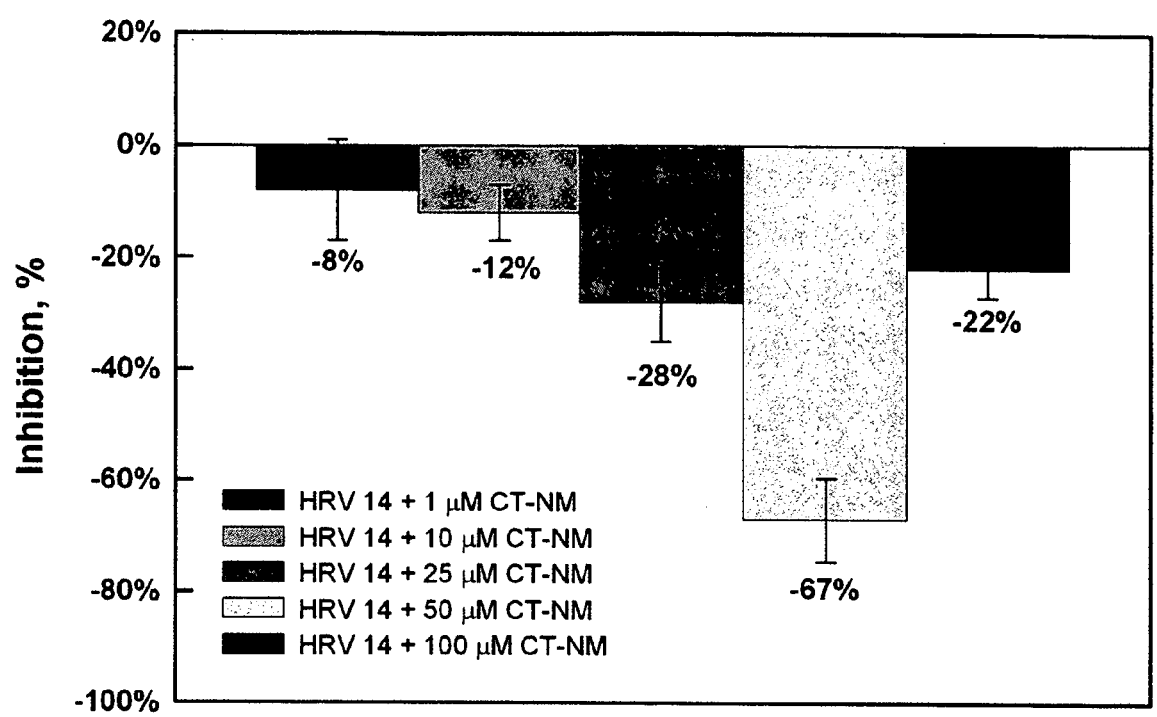
FIG. 30: Inhibition of human rhinovirus 14 (HRV14) induced CPE in HeLa cells by CapsiVirol-T NM; m.o.i., 0.1, effects measured 2 d.p.i, XTT test.
Figure 31:
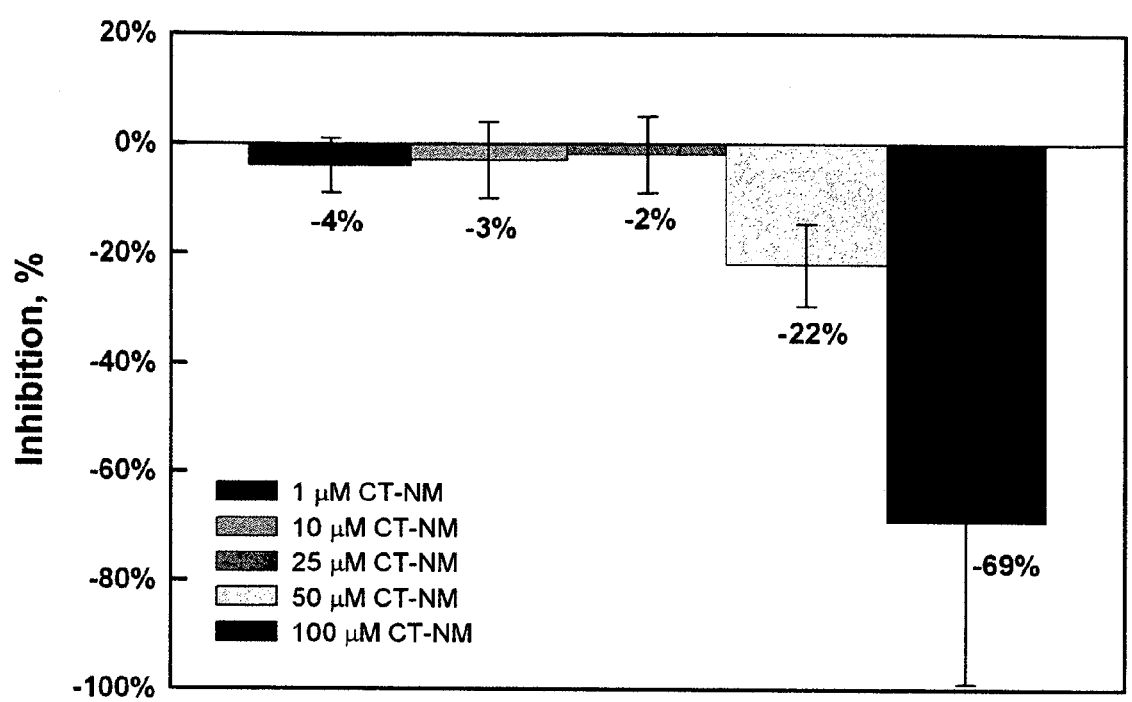
FIG. 31: Toxicity of CapsiVirol-T NM in HeLa cells; d p.i.=2, XTT test.
Figure 32:
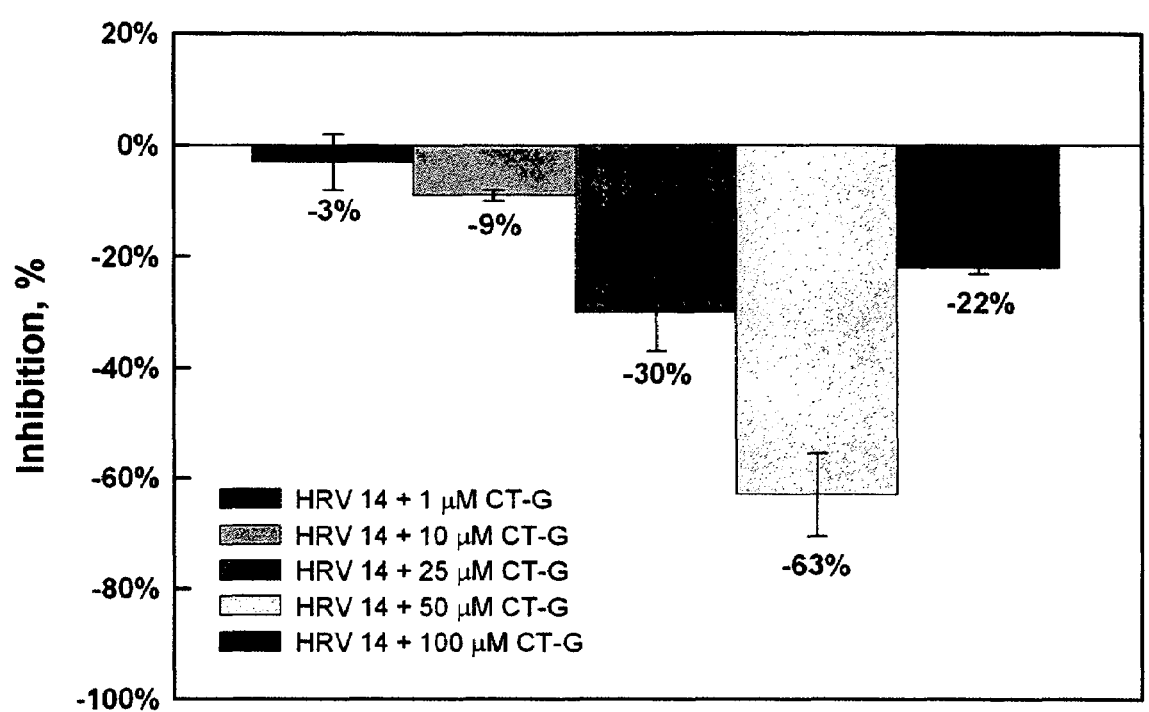
FIG. 32: Inhibition of human rhinovirus 14 (HRV14) induced CPE in HeLa cells by CapsiVirol-T G 25:1 (Capsol-T 25); m.o.i. 0.1, d.p.i. 2, CG=CapsiVirol-TG 25:1.
Figure 33:
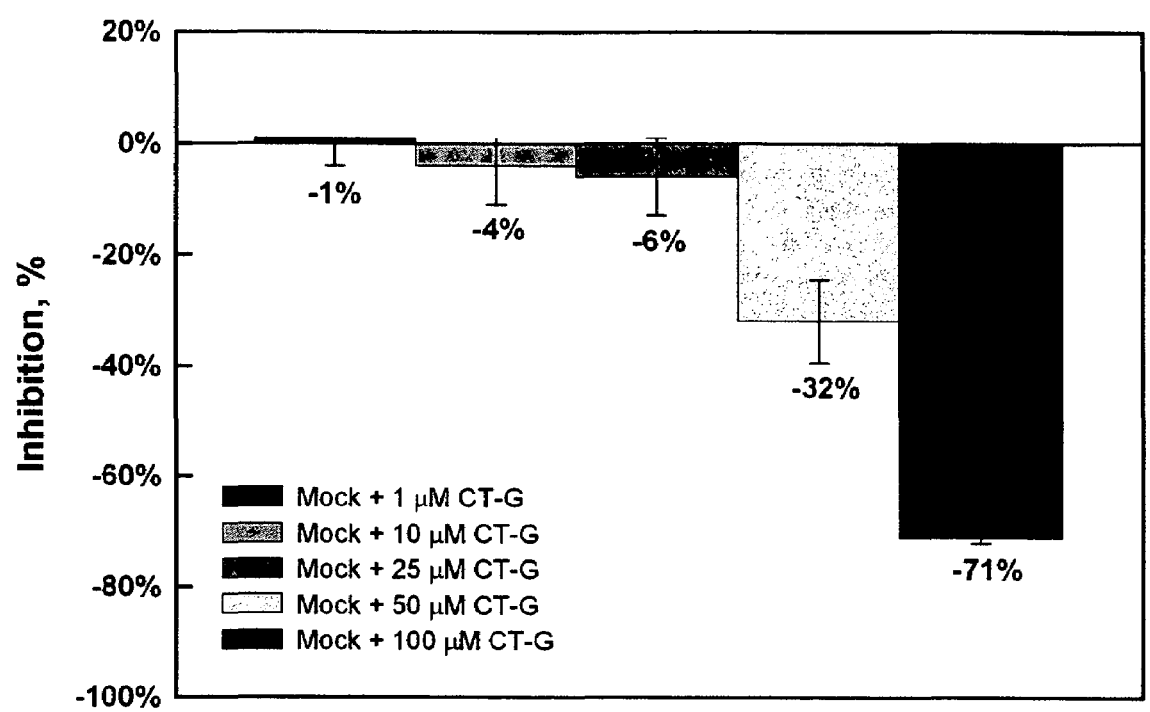
FIG. 33: Toxicity of CapsiVirol-T G 25:1 (Capsol-T 25) in HeLa cells; d.p.i. 2, CG=CapsiVirol-TG 25:1.
Figure 34:
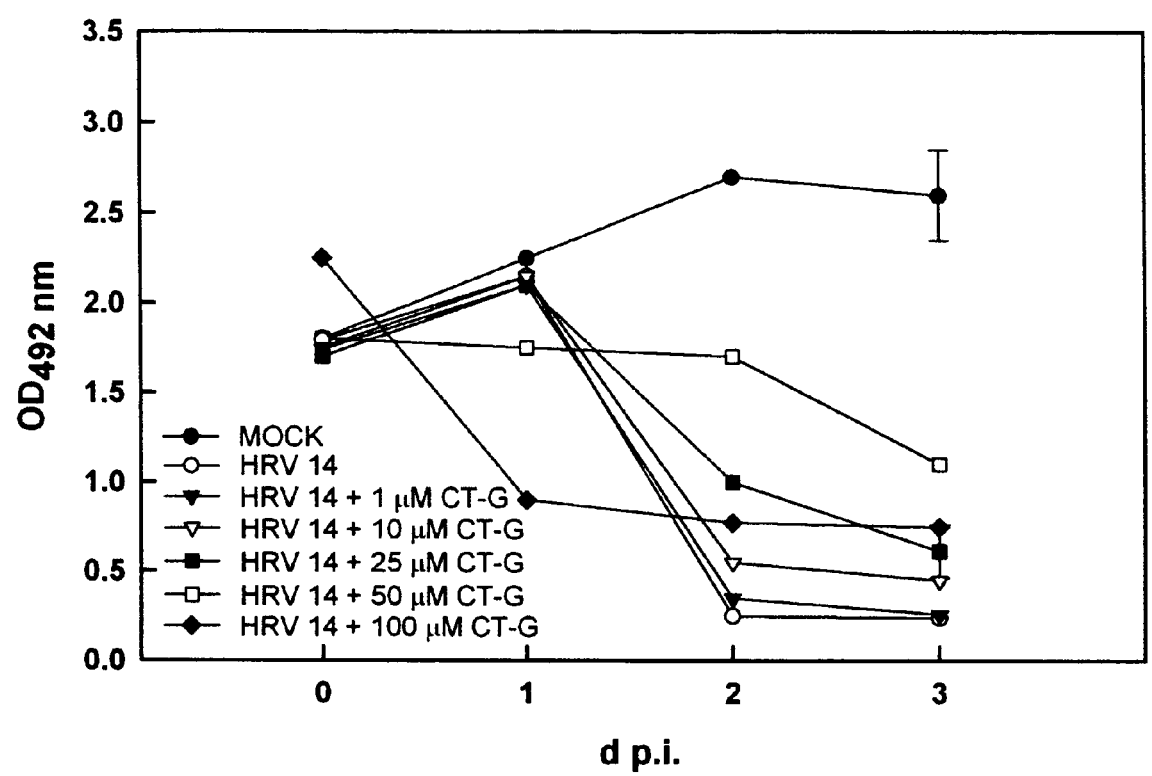
FIG. 34: Inhibition of human rhinovirus 14 (HRV14) induced CPE in HeLa cells by CapsiVirol-T G 25:1 (Capsol-T 25); m.o.i. 0.1; V+10 μM CT-G+Virus+CapsiVirol-T G, 25:1, CT-6=CapsiVirol-TG 25:1. XTT test.
Figure 35:
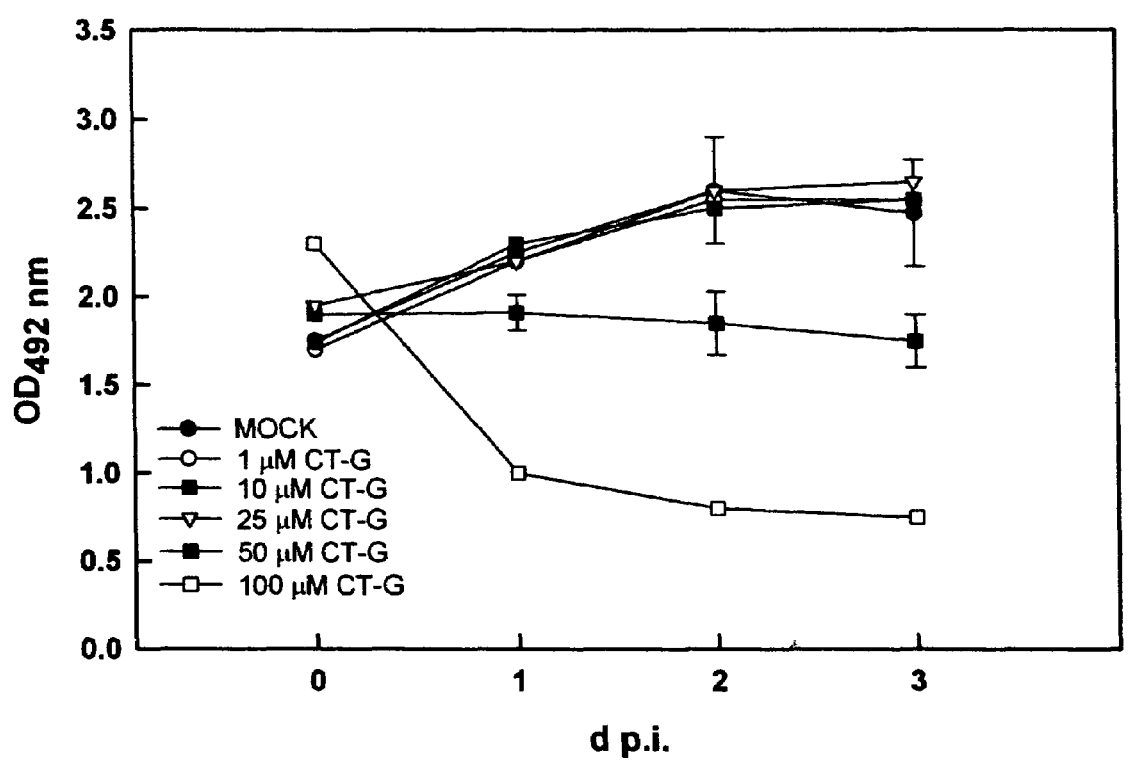
FIG. 35: Toxicity of CapsiVirol-T G 25:1 (Capsol-T 25) in HeLa cells; CT-G=CapsiVirol-T G 25:1, XTT test.

Example 4 vNOX Activity and Cytopathic Effect of HRV in MCF-10A Cells is Inhibited by Recombinant Antibody to tNOX With the recombinant single chain antibody (scFv) specific to tNOX and to vNOX, cytopathic effects were inhibited at a dilution of 1:170,000 (FIG. 26). In the corresponding enzymatic assay, VNOX activity was inhibited at a dilution of scFv of 1:200,000. The scFv reagent is remarkably effective in inhibiting both the cytopathic effect of HRV and in blocking vNOX activity.

Example 5

CapsiVirol-T Inhibition of vNOX is Reversible

We also used the vNOX assay to determine reversibility of CapsiVirol-T inhibition. CapsiVirol-T inhibition at the $EC_{50}$ was reversed completely by washing the cells with CapsiVirol-T-free PBS.

Example 6

Potential Anti-Cold Treatments Other than CapsiVirol-T

We have tested a number of substances of interest with the vNOX activity assay as summarized in Table III. The NSAIDS (Ibuprofen and naproxen) and acetaminophen inhibited with $EC_{50}$s in the micromolar range. The dose-response was very steep, however, with an EC50 near 10 μM. Pure EGCg was about as effective as CapsiVirol-T ($EC_{50}$ of 10 nM).

The effectiveness of zinc was surprising. However, $ZnCl_2$ gave an unusual dose response in both experiments. There was a initial inhibition that reached the $EC_{50}$ at about 10 nM and then plateaued up to 1 μM after which log dose-dependent inhibition resumed.

Example 7

Interactions of Potential Cold Products

The vNOX activity assay was used to examine combinations of potential cold preventatives and/or therapeutics. With a 1:1 mixture of CapsiVirol-T and $ZnCl_2$ there was enhancement of inhibition with a new $EC_{50}$ of about 1 nM.

There was a positive interaction between zinc and CapsiVirol-T (Table IV). Combination of zinc with CapsiVirol-T might give a marketing advantage, but it may be difficult to use zinc therapeutically. There is apparently very little, if any, free zinc in the body. Providing extra zinc seems to have little or no effect, despite in vitro results that may show profound responses.

In growth experiments (experiments with cells), we saw synergy between CapsiVirol-T and $ZnCl_2$ in inhibition with mouse mammary 4T1 cells. Two concentrations of CapsiVirol-T (5 and 10 μM) and 5 concentrations of $ZnCl_2$ (100 nM-1 mM) were tested. With HeLa cells there was synergy at high zinc concentrations but the response at low zinc concentrations was only additive. At equimolar concentrations, the $ZnCl_2$ and CapsiVirol-T were antagonistic with HeLa cells.

Also observed to inhibit the vNOX of MCF-10A cells were an *Echinacea* extract, capsaicin and vanillylamine (Table V). Vanillylamine, the putative active principle of CapsiVirol-T with an $EC_{50}$ of 0.1 nM, was the most active single substance thus far tested. It is understood that analogs of vanillylamine ($C_6$ to $C_{12}$) similarly inhibit vNOX.

Interestingly, growth experiments with CapsiVirol-T and *Echinacea* also showed synergy in inhibition with both HeLa and mouse mammary 4T1 cells. Two concentrations of CapsiVirol-T (5 and 10 M) and 5 concentrations of *Echinacea* (an infusion of 2.5 mg/2 ml undiluted and diluted 1:10, 1:100; 1:1000 and 1:10,000) were tested.

Example 8

Evaluation of CapsiVirol-T for Cold Prevention and/or Treatment

Packets of 350 mg capsules of CapsiVirol-T were distributed to 6 groups of individual volunteers near the end of the winter cold season. Participants were instructed to take a capsule at the first sign of a cold and subsequent capsules at 4 h intervals as needed. Participants were asked to rank their response as (1) better (2) no change (3) worse. Age groups were A: 15-30 y; B: 30-60 y; C: >60 y.

One group C male took 55 capsules of Capsi-Virol-T during a period of several months. For the most part, significant relief occurred within 20 to 40 min of taking the capsule. Despite sporadic bouts of morning or late evening sneezes and sniffles, a full blown cold was averted during the test period. These were consistent findings reported by all those who participated in the study.

An additional male, age group B, with severe respiratory allergies took 24 capsules with no alleviation of symptoms.

Example 9

IL-8 Induction in Response to HRV14 Infection and CapsiVirol-T

IL-8 induction in response to HRV14 infection and CapsiVirol-T was estimated using a commercially-available kit (Table 6). HRV14 infection stimulated IL-8 production. The HRV-stimulated IL-8 production was not reduced by CapsiVirol-T. On the contrary, a variable, 30% overall but statistically insignificant stimulation of IL-8 in response to CapsiVirol-T was observed.

Example 10

Other Viruses

In addition to HRV14 and HIV, the effect of EGCg on virus infection was tested with Poliovirus 1 in HeLa cells; Coxsackievirus b3 in HeLa cells; TMEV/GDVII virus in RAW macrophages; TMEV/Bean virus in RAW macrophages; Herpes simplex virus 1 in HeLa cells. TMEV is Theiler's murine encephalomyelitis virus. Infection was prevented for Herpes simplex and Theiler's murine encephalomyelitis virus, but the $EC_{50S}$ were 100 to 1000 times greater than for RHV 14 or HIV-1.

EGCg also was impressively effective in reducing infectivity of HIV in human MT-2 cells grow in culture or peripheral blood monocytes (PBMCs) obtained from healthy donors. Effectiveness was proportional to titer of infective virus particles with an $EC_{50}$ of near 1 μM with a control virus production of 14,000 infective particles/ml and near 10 μM with a control virus production of 40,000 infective particles/ml. When the supernatants on day 4 from the experiment were reassayed with a second group of MT-2 cells based on syncytia formation after 5 days (a biological measure of infective virus particles), the $EC_{50}$ for prevention of infection was near 0.1 μM and at 1 μM infectivity was almost entirely prevented.

The principal green tea catechin EGCg has been reported by others as a candidate HIV agent (Freedman, R. B. (1989) Cell 57: 1069-1072; Passina et al. (2002) AIDS 16: 939-941) based on laboratory tests similar to those we have conducted. Clinical trials have not been carried out to our knowledge. An inhibition of infectivity of influenza virus by tea polyphenols also has been reported (Yamaguchi et al., 2002, Antiviral Res. 53: 19-34).

Figure 27:
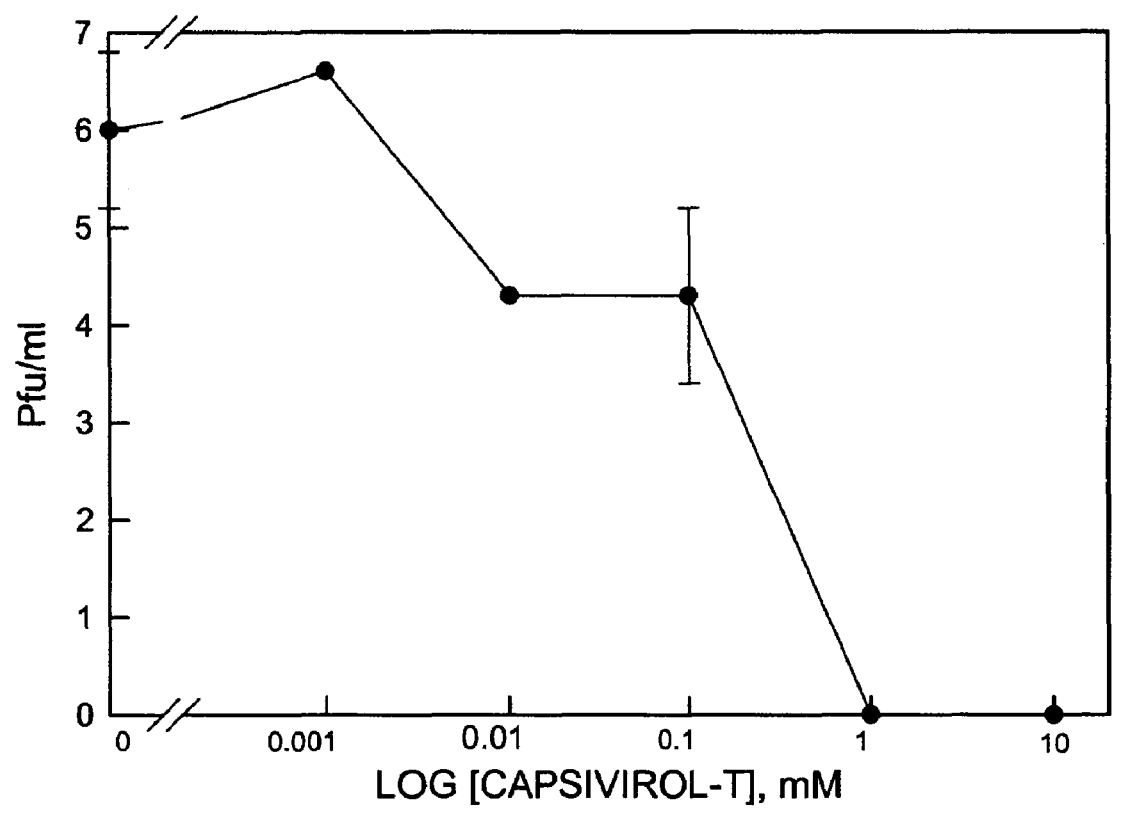

Additionally, CapsiVirol-T was assayed in a BHK-yellow fever virus assay system (FIG. 27). Protection was afforded, but the concentrations required were in the low millimolar (high micromolar) range. Studies were also carried out with the SV 40-infected 3T3 cells mentioned above.

Example 11

Possible Role of vNOX in Rhinovirus Assembly

Evidence suggests that in contrast to HIV, for example, the CapsiVirol-T needs to be present both during and after infection for the greatest effectiveness. Current models suggest that rhinovirus assembly takes place within the infected cell at the cytosolic surface of an internal membrane system. Recent findings from our laboratory show localization of a tNOX-like enzymatic activity associated with the cytosolic surface of such membranes of HeLa cells (as well as at the exterior surface of the plasma membrane).

A tNOX-like 29 kDa protein (designated vNOX) and an associated ECTO-NOX activity were shown to be rapidly induced in non-cancer MCF-10A mammary epithelial cells upon infection with HRV14 and HRV16.

The HRV14-induced vNOX enzymatic activity was blocked both by a recombinant antibody (anti-tNOX scFv) to tNOX and by a green tea catechin-*Capsicum* mixture (CapsiVirol-T), which was 10 times more effective than EGCg alone and at least 100 times more effective than green tea alone in protecting cells against the cytopathic effects of HRV14 infection.

The HRV14-induced vNOX differed from classical tNOX in several important respects. The HRV14-induced vNOX was not shed from the cell surface. The HRV14-induced vNOX exhibited an apparent MW on SDS-PAGE of 29 kDa (apparent MW of tNOX is 34 kDa). The HRV-induced vNOX was resistant to inhibition by reduced glutathione, whereas tNOX activity was inhibited by reduced glutathione.

The dose-dependence in the ablation of HRV14-induced cytopathic effects in HeLa cells and the inhibition of HRV14-induced vNOX of HRV14-infected MCF-10A cells were indistinguishable, suggesting a cause and effect relationship. The $EC_{50}$ for ablation of the cytopathic effect by CapsiVirol-T was equivalent to 10 nM EGCg, whereas the $EC_{50}$ for inhibition by the anti-tNOX scFv was at a dilution of 1:170,000.

Example 12

Inhibition of vNOX Activity of HRV14 Infected MCF-10A Cells by CapsiVirol-T was Reversible The cytopathic effects of HRV14-infected human osteoblast (hFOB) cells were ablated by CapsiVirol-T and the recombinant anti-tNOX antibody in a manner similar to that of the MCF-10A cells. The $EC_{50}$ for inhibition by CapsiVirol-T was 1 nM. With the recombinant anti-tNOX scFv, the cytopathic effect was inhibited with an $EC_{50}$ at a dilution of $1:1.2 \times 10^7$.

The cytopathic effects of HRV14-infected human cervical carcinoma (HeLa) cells was ablated by CapsiVirol-T and by the recombinant anti-tNOX antibody. Because HeLa cells are cancer cells, the estimates were complicated by cytotoxicity.

The experiments with HeLa cells were repeated with a HeLa line from the Free University of Berlin where the CapsiVirol-T was less cytoxic. An $EC_{50}$ of 35 µM was observed in two experiments with a cytotoxicity of only 6% to unequivocally demonstrate a response of the HRV14 infection in HeLa cells to CapsiVirol-T.

A rapid, sensitive and reproducible spectrophotometric assay was developed for HRV14-induced vNOX of 72 h-infected MCF-10A cells. The assay based on inhibition of induced vNOX activity paralleled that of the inhibition of the cytopathic effects.

The spectrophotometric assay was utilized in parallel with cytopathic effect on MCF-10A cells to evaluate different substances with potential anti-colds activity. Comparisons were to CapsiVirol-T with an $EC_{50}$ of 10 nM and the anti-tNOX scFv which inhibited by 50% at a dilution of 1:200,000. NSAIDS (Ibuprofen and Naproxen) inhibited with $EC_{50}$ in the micromolar range of concentrations (Table 3). Acetaminophen inhibited with an $EC_{50}$ of 1 µM, $ZnCl_2$ inhibited with an $EC_{50}$ of 10 nM, and EGCg inhibited with an $EC_{50}$ of 10 nM. *Echinacea* infusion (2.5 mg/2 ml water) inhibited with the $EC_{50}$ at a dilution of 1:100,000 (Table V). The effectiveness of CapsiVirol-T was enhanced approximately 10-fold by combination with $ZnCl_2$ and Naproxen (1:1 molar ratios) or *Echinacea*. Interestingly, the CapsiVirol-green tea synergy of CapsiVirol-T could not be duplicated by a cayenne pepper-green tea mixture optimized for anticancer activity.

A positive correlation between taking a single 350 mg capsule of CapsiVirol-T and reduction in common cold symptoms was obtained in 10 individuals reporting in an informal human trial. Most commonly significant relief occurred within 20 to 40 min, and overt colds were averted.

The results reported herein demonstrate that the HRV14-induced vNOX activity is a viable antiviral target. The spectrophotometric assay provides for rapid and reproducible evaluations even of very complex mixtures.

CapsiVirol-T exhibits a marked activity as a cold preventative, based on inhibition of HRV14-induced VNOX, cytopathic effects in MCF-10A, hFOB and HeLa cells and in human subjects.

Various *Capsicum* (pepper) preparations were evaluated for combination with standardized green tea extract (decaffeinated). For the latter, a standardized beverage grade, water soluble and decaffeinated green tea extract containing 92% (w/v) polyphenols, of which 80% were catechins with the following composition: 50% epigallocatechin-3-gallate (EGCg), 6% epicatechin (EC), 15% epicatechingallate (ECG, 5% epigallocatechin (EGC) and 2% gallocatechin gallate (GCG). The caffeine content was less than 1%. Several commercial preparations were evaluated that met the standardized composition and efficacy requirements.

Approximately 12 commercially available pepper species (pepper powders, *Capsicum*) with thin pericarps (necessary for drying) and varying Pcin (pungent principle) contents were evaluated. Species with high capsaicin contents were treated enzymatically with amidases and/or general food grade hydrolases or other hydrolytic procedures to reduce discomfort prior to testing. Both *Capsicum fructescens* and *Capsicum annuum* varieties were evaluated. Several varieties were found with the required physical and efficacy characteristic necessary to exert synergy with the standardized decaffeinated green tea extract as a cold preventative. Many pepper preparations are available commercially (powdered, food grade). Sourcing does not appear to be an important factor in determining effectiveness.

Example 13

Food-grade CapsiVirol-T Formulations

The new CapsiVirol-T formulation designated as CapsiVirol-T (FG) for food grade, was compared to a CapsiVirol-T formulation of 25 parts lyophilized green tea extract to one part enzymatically-treated African bird pepper (*Capsicum fructescens*) extract in standard laboratory rhinovirus assays.

Inhibition of the vNOX cell surface target protein expressed during rhinovirus infection was studied. In in vitro assays, rhinovirus-infected MCF-10A (human mammary, non-cancer epithelia) expressing high levels of vNOX were evaluated to compare CapsiVirol-T and CapsiVirol-T (FG). The new food grade formulation at a ratio of 25 or 50 parts green tea extract to 1 part pepper powder was equivalent or superior to the standard CapsiVirol-T formulation consisting of 25 parts green tea extract to 1 part enzymatically-treated African bird pepper (*Capsicum fructescens*) extract.

Example 14

Inhibition of Cytopathic Effects in Human Cultured Cell Lines

In the standard assay (for ablation of the cytopathic effects of human rhinovirus in MDF-10A cells), CapsiVirol-T (FG) was found to be equivalent to standard CapsiVirol-T. Cytopathic effects of human rhinovirus 14 were also studied in HeLa cells. The results of this study validate the efficacy of CapsiVirol-T (FG) compared to standard CapsiVirol-T.

A CapsiVirol-T (FG) product was formulated by tumbling the following dry ingredients in the noted relative amounts: CapsiVirol-T (FG) 350.0 mg, Solkaflor 75.0 mg, Mg Stearate 6.4 mg, and Syloid Silica Gel 6.4 mg (Net wt. 437.8 mg). The material was then encapsulated in gelatin capsules (350 mg per capsule).

In anecdotal intervention trials, approximately 100 of the 350 mg gelatin capsules were taken by volunteers at the first signs of cold symptoms during fall and winter cold seasons. In most cases, volunteers experienced ablation of symptoms (clearing of nasal passages, drying of "runny nose", sneezing reduced or eliminated) followed by cessation of cold progression. Several individuals taking CapsiVirol-T (FG) on a regular basis were cold-free for the entire season. Once a cold has developed, the product does not eliminate symptoms, but it may accelerate the recovery and prevent recurrence.

A dosage form and amount has been established. A capsule size containing 350 mg of CapsiVirol-T (FG) appears sufficient. One 350 mg capsule per day seems to have a clear preventive effect or 1 capsule at cold symptom onset plus 1 additional capsule at 4 h intervals (based on pharmacokinetics) thereafter is the currently recommended dosage regimen to achieve the benefits desired based on three seasons of anecdotal testing.

While 350 mg dosages have been tested, the capsules or tablets can comprise from about 100 to about 750 mg of the CapsiVirol-T (FG). In addition, while there are specifically exemplified formulations, each dosage can contain the active ingredients at ratios of from about 15 to about 75 parts green tea extract to 1 part pepper powder, desirably from 25 to 50 parts green tea extract to 1 part pepper powder.

TABLE 1

Inhibition by 10-100 nM CapsiVirol-T of the cytopathic effect of HRV14 (1:40 dilution) on HeLa cells.

| Treatment | % Inhibition of cytopathic effect |
|---|---|
| Before infection (1 h) | <2 |
| During infection (1 h) | 32 |
| During (1 h) and after infection (72 h) | 48 |

TABLE 2

Cytopathic effect after 72 h of human hFOB osteoplasts in response to HRV-infection.

| Virus dilution | Cytopathic effect, % |
|---|---|
| No virus | 10 ± 5 |
| 1:70 | 20 ± 10 |
| 1:50 | 22 ± 5 |
| 1:20 | 37 ± 9 |

TABLE 3

Inhibition of vNOX enzymatic activity of 73 h hrv-infected MCF-10A cells grown in culture.

| Substance | $EC_{50}$ Cell Production I (Mar. 24, 2003) | $EC_{50}$ Cell Production II (Apr. 01, 2003) |
|---|---|---|
| CapsiVirol T | 10 nM/10 nM | |
| Anti-tNOX scFv | 1:200,000 | |
| Ibuprofren | 1 µM | |
| ZnCl$_2$ | 10 nM | 10 nM |
| Naproxin | 5 µM | 2 µM |
| Acetaminophin | 1 µM | |
| EGCg | | 10 nM |

TABLE 4

Inhibition of vNOX enzymatic activity of 72 h HRV-infected MCF-10A cells grown in culture.

| Substance* | $EC_{50}$ Cell Production II (Apr. 01, 2003) | $EC_{50}$ Cell Production III (Apr. 15, 2003) |
|---|---|---|
| CapsiVirol-T + ZnCl$_2$ | 1 nM | 1 nM |
| CapsiVirol-T + Naproxin | | 1 nM |
| Green Tea + Cayenne (20:1) | | 100 nM |
| Green Tea + Cayenne (20:1) + Capsibiol (50:1) | | 10 nM |

*1:1 Molar ratio

TABLE 5

Inhibition of vNOX activity of 72 h HRV-infected MCF-10A cells grown in culture.

| Substance | $EC_{50}$ Cell Production IV (May 01, 2003) |
|---|---|
| *Echinacea* | 1:100,000* |
| Capsaicin | 1 nM |
| Vanillylamine | 0.1 nM |

*2 g *Echinacea* (Nature's Resource) extracted in 2.5 ml near boiling water for 10 min. Particulate matter was removed and the supernatant was tested.

TABLE 6

Response of IL-8 of HeLa cells to HRV infection and effect of CapsiVirol-T added during and post infection. After 72 h. Average of 2 determinations ± mean average determination from 1 of 3 experiment with consistent results.

| Conditions | pg/ml |
|---|---|
| Cells | 10 ± 2 |
| Cells + HRV14 | 60 ± 15 |
| Cells + 10 µM CapsiVirol-T | 80 ± 5 |
| Cells + HRV 14 + 10 µM CapsiVirol-T | 90 ± 3 |
| Cells + 100 µM CapsiVirol-T | 80 ± 10 |

TABLE 6-continued

Response of IL-8 of HeLa cells to HRV infection and effect of CapsiVirol-T added during and post infection. After 72 h. Average of 2 determinations ± mean average determination from 1 of 3 experiment with consistent results.

| Conditions | pg/ml |
| --- | --- |
| Cells + HRV14 + 100 μM CapsiVirol-T | 120 ± 32 |

TABLE 7

Responses to CapsiVirol-T

| Participant No. | Sex | Age Group | Number of Capsules | Average Efficacy Rating |
| --- | --- | --- | --- | --- |
| 1 | M | C | 55 | 1.3 |
| 2 | F | C | 3 | 1.3 |
| 3 | F | C | 12 | 1.0 |
| 4 | M | B | 24 | 1.1 |
| 5 | F | B | 4 | 1.0 |
| 6 | M | A | 3 | 1.0 |
| 7 | F | B | 12 | 1.6 |
| 8 | M | A | 1 | 1.0 |
| 9 | M | C | 2 | 1.0 |
| 10 | M | C | 1 | 1.0 |

We claim:

1. A method for treating a viral infection in a mammal in need thereof, said method comprising administering to the mammal a composition comprising tea catechins and vanilloids, in amounts effective to reduce incidence of virus infection and/or to kill virus-infected cells, wherein the ratio of EC to EGCg concentration in said tea catechins is from about 10:1 to about 100:1.

2. The method of claim 1, wherein the tea catechins and vanilloids are supplied in a ratio of from 25:1 to 50:1 in the form of food or beverage grade tea extract and *Capsicum* powder respectively.

3. The method of claim 2, wherein the *Capsicum* is cayenne, bell, poblano, serrano, jalapeno, guajillo, New Mexican, Anaheim, Tabasco or African bird pepper.

4. The method of claim 2, wherein the virus infection is *rhinovius* casual to the common cold or a human immunodeficiency virus infection and wherein the mammal is human.

5. A method for treating a viral infection in a mammal in need thereof, said method comprising administering to the mammal thereof a composition comprising tea catechins adjunctively with a composition comprising vanilloids, wherein the amounts of the catechins and vanilloids administered are effective to treat virus infection and/or to kill virus-infected cells, wherein the ration of EC to EGCg concentration in said tea catechins is from about 10:1 to about 1000:1.

6. The method of claim 5, wherein the catechins and vanilloids are supplied in a ration of from 25:1 to 50:1 in the form of a food or beverage grade tea extract and *Capsicum* powder respectively.

7. The method of claim 6, wherein the viral infection is a *rhinovirus* infection or a human immunodeficiency virus infection and wherein the mammal is human.

8. The method of claim 6, wherein the virus infection is a influenza virus A, influenza virus B, herpes virus, yellow fever virus or Theriler's murine encephalomyelitis virus infection.

* * * * *